United States Patent
Smith et al.

(10) Patent No.: US 6,887,839 B2
(45) Date of Patent: *May 3, 2005

(54) SOLID ALKYLBENZENE SULFONATES AND CLEANING COMPOSITIONS HAVING ENHANCED WATER HARDNESS TOLERANCE

(75) Inventors: George A. Smith, Austin, TX (US); Samir S. Ashrawi, Austin, TX (US); Raeda M. Smadi, Round Rock, TX (US); Prakasa R. Anantaneni, Austin, TX (US)

(73) Assignee: Huntsman Petrochemical Corporation, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/370,144

(22) Filed: Feb. 19, 2003

(65) Prior Publication Data

US 2003/0186831 A1 Oct. 2, 2003

Related U.S. Application Data

(62) Division of application No. 09/559,841, filed on Apr. 26, 2000, now Pat. No. 6,562,776, and a continuation-in-part of application No. 08/879,745, filed on Jun. 20, 1997, now Pat. No. 6,315,964, and a continuation-in-part of application No. 08/598,692, filed on Feb. 8, 1996, now Pat. No. 5,847,254, which is a division of application No. 08/598,695, filed on Feb. 8, 1996, now Pat. No. 5,770,782.
(60) Provisional application No. 60/178,823, filed on Jan. 28, 2000.

(51) Int. Cl.$^7$ ............................................. C11D 17/00
(52) U.S. Cl. ...................... 510/352; 510/357; 510/424; 510/426; 510/492
(58) Field of Search ................................. 510/352, 357, 510/424, 426, 492

(56) References Cited

U.S. PATENT DOCUMENTS 4,162,236 A * 7/1979 Feierstein et al. .......... 510/352

OTHER PUBLICATIONS

Rubinfeld, Joseph, E.M. Emery and D. Cross "Structure and Performance Property Relations of Straight–Chain Alkylbenzenes"vol. 4, Mar. 1965.*

* cited by examiner

*Primary Examiner*—Necholus Ogden
(74) *Attorney, Agent, or Firm*—Christopher J. Whewell

(57) ABSTRACT

This invention is directed to detergent compositions which employ sulfonated linear alkylbenzenes as surfactants, wherein the sulfonated linear alkylbenzenes have a higher content of the sulfonated 2-phenyl alkylbenzene isomers than was previously available in sulfonated phenyl alkylbenzene surfactants of the prior art. Cleaning compositions according to the invention are more effective as cleaning agents over their counterparts of prior art which contain sulfonated linear alkylbenzenes having lower contents of the 2-phenyl alkylbenzene isomers, owing to an unexpected increase in tolerance of water hardness minerals normally associated with precipitation of the active detergent agent. Solid sulfonate salts of alkylbenzenes are also provided, including dry formulations containing same.

19 Claims, 8 Drawing Sheets

SOLID ALKYLBENZENE SULFONATES AND CLEANING COMPOSITIONS HAVING ENHANCED WATER HARDNESS TOLERANCE

This application is a continuation-in-part application of U.S. application Ser. No. 08/598,692, filed Feb. 8, 1996 now U.S. Pat. No. 5,847,254 and of U.S. application Ser. No. 08/879,745, filed Jun. 20, 1997, now U.S. Pat. No. 6,315,964, which was a divisional of Ser. No. 08/598,695, filed Feb. 8, 1996, now U.S. Pat. No. 5,770,782, and of U.S. application Ser. No. 09/559,841 filed Apr. 26, 2000 now U.S. Pat. No. 6,562,776, and U.S. Provisional Application No. 60/178,823 filed Jan. 28, 2000, the contents of each of which are expressly incorporated herein by reference.

BACKGROUND OF THE INVENTION

This invention relates generally to detergent compositions and cleaning compositions having enhanced detergency and cleaning capabilities. It relates more particularly to detergent and cleaning compositions containing the 2-phenyl isomer of linear alkylbenzene sulfonates in concentrations higher than were previously available in the prior art, owing to the discovery of the revolutionary catalyst and process for producing such isomers in high concentration, as detailed herein.

Chemical compounds useful for removing grease, oils, dirt and other foreign matter from various surfaces and objects have been known for some time, including the simple soaps which are manufactured by the saponification of oils (including animal fats and vegetable oils). Saponification is essentially a process whereby aqueous alkali metal hydroxide is mixed with an ester (such as an animal fat or vegetable oil) to cause de-esterification of the ester with the formation of the alkali salt(s) of the carboxylic acid(s) from which the ester was derived, which salt(s) are typically very soluble in aqueous media. Importantly, the anion portions of such alkali salts of the carboxylic acid(s) include as part of their molecular structure a hydrophilic portion, i.e., the carboxylate function, which is highly attracted to water molecules. Such salts also include a hydrophobic portion as part of their molecular structure, which is typically a hydrocarbon-based portion containing between about 12 and 22 carbon atoms per molecule. Such salts are commonly referred to by those skilled in the art as "salts of fatty acids", and are often commonly referred to by laypersons as "soap". Aqueous solutions of salts of fatty acids are very effective at causing grease, oils, and other normally water-insoluble materials to become soluble and thus capable of being rinsed away, thus leaving behind a clean substrate which may typically comprise a tabletop, countertop, article of glassware or dinnerware, flatware, clothing, architecture, motor vehicle, human skin, human hair, etc.

While the industries for the production of such soaps from fats and oils are now well-established, saponification chemists and other workers have continuously sought improved chemistry for rendering materials which are not normally soluble in aqueous media to become soluble therein. Towards this end, a wide variety of materials have been identified by those skilled in the art, with the common denominator of such materials being that the materials all contain a hydrophobic portion and a hydrophilic portion in their molecular structures.

One family of materials that have been identified as suitable soap substitutes are the linear alkylbenzene sulfonates ("LAB sulfonates"). The LAB sulfonates in general are exemplified as comprising a benzene ring structure having a hydrocarbyl substituent (or "alkyl substituent") and a sulfonate group bonded to the ring in the para position with respect to one another. The length of the hydrocarbon chain of the alkyl substituent on the ring is selected to provide a high level of detergency characteristics while the linearity of the hydrocarbon chain enhances the biodegradability characteristics of the LAB sulfonate. The hydrocarbyl substituent may typically contain 6, 7, 8, 9, 10, 11, 12, 13, 14 or 15 carbon atoms (the "detergent range") in a substantially linear arrangement, and may be attached to the benzene ring through a conventional Friedel-Crafts alkylation process using a corresponding olefin and employing a Lewis acid catalyst such as aluminum chloride and conditions known to those skilled in the art as useful for such alkylations. Various alkylation processes useful for production of alkylbenzenes are described in U.S. Pat. Nos. 3,342,888; 3,478,118; 3,631,123; 4,072,730; 4,301,316; 4,301,317; 4,467,128; 4,503,277; 4,783,567; 4,891,466; 4,962,256; 5,012,021; 5,196,574; 5,302,732; 5,344,997; and 5,574,198, as well as European patent application 353813 and Russian patent 739,046, the entire contents of which are incorporated herein by reference thereto.

Once a hydrocarbyl radical has been appended to a benzene ring in accordance with the foregoing, the resulting linear alkylbenzene must subsequently be sulfonated in order to produce a finished detergent material that is capable of solubilizing grease, oils, dirt, and the like from various substrates, such as dishes, motorized vehicles, hard surfaces, architecture, and fabrics, to name but a few. Sulfonation is a known chemical process whose reactants and conditions are known to those skilled in the chemical arts. Through the process of sulfonation, a sulfonate group is caused to become chemically bonded to a carbon atom in the benzene ring structure of the linear alkylbenzene, thus providing the molecule as a whole with a hydrophilic sulfonate group in addition to the hydrophobic hydrocarbyl portion.

It is known that during the course of mono-alkylation of the benzene ring to introduce a hydrocarbon tail into the molecular structure, several structural isomers are possible in which the benzene ring is attached to various points along the hydrocarbon chain used. It is generally believed that steric effects of the mono-olefin employed play a role in the distribution of isomers in the mono-alkylated product, in addition to the catalyst characteristics and reaction conditions. Thus, it is possible for a single benzene ring to become attached to, say, the 2, 3, 4, or 5 positions in a 10 carbon atom linear mono-olefin, with a different alkylbenzene isomer being produced in each such case. Sulfonation of such different materials results in as many different alkylbenzene sulfonates, each of which have different solubilization capabilities with respect to various oils, grease, and dirt, etc.

The sulfonates of the 2-phenyl alkyl isomers are regarded by those skilled in the art as being very highly desirable materials, as sulfonated linear alkylbenzene detergent materials made from sulfonation of the 2-phenyl alkyl materials have superior cleaning and detergency powers with respect to the sulfonation products of other isomers produced during the alkylation. The general structure of the most desired 2-phenyl alkyl isomer products may be defined as:

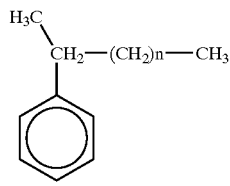

which in a preferred embodiment has n equal to any integer selected from the group consisting of: 5, 6, 7, 8, 9, 10, 11, and 12. Since the Friedel-Crafts type alkylation employed to produce 2-phenyl alkyl isomers according to the invention may often utilize a mixture of olefins in the detergent range ($C_8$ to $C_{15}$), a distribution of various alkylbenzenes results from such alkylation. The present invention is therefore in one broad respect concerned with the use of sulfonated 2-phenyl alkylbenzenes derived from the alkylation of benzene, preferably using α-mono olefins having a carbon number distribution in the detergent range, in detergent formulations.

As mentioned above, a 2-phenyl alkylbenzene is but one possible structural isomer resulting from the alkylation of benzene with an olefin, and a mixture of 2-phenyl alkylbenzenes results from the alkylation of benzene using as reactants a feed which includes a mixture of olefins in the detergent range. This may be due to resonance stabilization which permits effective movement of the double bond in an activated olefin/Lewis acid complex. Generally speaking, the collection of all isomeric products produced from the alkylation of benzene with a mixture of olefins in the detergent range is commonly referred to by those of ordinary skill in the art as "linear alkylbenzenes", or "LAB's". Frequently, those skilled in the art use "linear alkylbenzenes" or "LAB's" interchangeably with their sulfonates. It is common for people to say LAB's when they are actually referring to sulfonated LAB's useful as detergents.

Typically, LAB's are manufactured commercially using classic Friedal-Crafts chemistry, employing catalysts such as aluminum chloride, or using strong acid catalysts such as hydrogen fluoride, for example, to alkylate benzene with olefins. While such methods produce high conversions, the selectivity to the 2-phenyl isomer in such reactions as known in the prior art is low, generally being about 30% or less. LAB's with a high percentage of the 2-phenyl isomer are highly desired because such compounds when sulfonated have long "tails" which provide enhanced solubility and detergent properties.

SUMMARY OF THE INVENTION

In one aspect the present invention provides a method and catalyst for LAB production having high substrate olefin conversion, high selectivity to 2-phenyl isomer LAB production, and employing a catalyst having long lifetimes and easy handling. Through use of this aspect of the invention, 2-phenyl alkylbenzenes may be produced in yields in excess of 80.0% on the basis of catalyst selectivity.

More importantly, the present invention provides detergent compositions and cleaning formulations made with a component that comprises a mixture of sulfonated alkylbenzenes in which the hydrocarbon groups that are bonded to the benzene ring may comprise any number of carbon atoms in the detergent range and in which at least 80% (weight basis) of the sulfonated alkylbenzene isomers present have the phenyl group attached to the hydrocarbon group in the 2 position of the hydrocarbon group. The invention provides detergent compositions and formulations which are formed from an alkylbenzene sulfonate component that comprises a mixture of: 1) a first alkylbenzene sulfonate component comprising 2-phenyl alkylbenzene sulfonates in which 2-phenyl alkylbenzene sulfonate isomers comprise at least 80% of all alkylbenzene sulfonate isomers present; and 2) a second alkylbenzene sulfonate component comprising either: a) alkylbenzene sulfonates in which isomers having the benzene ring attached to a linear alkyl group at a position other than the alkyl group's 2 position comprise at least 70% of all alkylbenzene sulfonate isomers present; or b) branched alkylbenzene sulfonates, or a combination thereof.

Branched alkylbenzene sulfonates may be introduced into a formulated product according to the invention in one of two ways. First, a portion of the linear olefin feedstock used in the alkylation reaction of the benzene ring may be replaced by branched olefin(s), to provide an alkylbenzenes mixture for sulfonation in which the alkylbenzenes contain a selected amount of branched alkylate. The second method of providing branched alkylbenzene sulfonates in a finished formulation according to the invention is when branched alkylbenzene sulfonates purchased on the open market are used as a blending component in the production of a finished product according to the invention. Thus, by either blending or providing branching in the alkylation reaction product, it is possible to provide a wide range of the amount of branched alkylbenzene sulfonates in a finished formulation according to the invention; however, it is preferable that the branched isomers comprise any amount less than 50.0% of the total alkylbenzene sulfonate isomers present in a given formulation according to the invention, in another preferred form of the invention, branched isomers comprise any amount less than 15.00% of the total alkylbenzene sulfonate isomers present in a given formulation according to the invention; in yet another preferred form of the invention, branched isomers comprise any amount less than 2.00% of the total alkylbenzene sulfonate isomers present in a given formulation according to the invention.

In one preferred form of the invention, lower activity isomers (isomers other than the 2-phenyl isomers) of linear alkylbenzenes are present in the second alkylbenzene sulfonate component in any amount between 0.00% and 70.00%, including every hundredth percentage therebetween, by weight based upon the total weight of the second alkylbenzene sulfonate component.

In a preferred form of the invention, the second alkylbenzene sulfonate component may comprise alkylbenzene sulfonates in which isomers having the benzene ring attached to a linear alkyl group at a position other than the alkyl group's 2 position comprise at least 50% of all alkylbenzene sulfonate isomers present.

In another preferred form of the invention, the second alkylbenzene sulfonate component may comprise alkylbenzene sulfonates in which isomers having the benzene ring attached to a linear alkyl group at a position other than the alkyl group's 2 position comprise at least 40% of all alkylbenzene sulfonate isomers present.

In another preferred form of the invention, the second alkylbenzene sulfonate component may comprise alkylbenzene sulfonates in which isomers having the benzene ring attached to a linear alkyl group at a position other than the alkyl group's 2 position comprise at least 30% of all alkylbenzene sulfonate isomers present.

Thus, an alkylbenzene sulfonate component according to yet another embodiment of the invention may contain sulfonated 2-phenyl alkylbenzenes in an amount of at least 30.00% by weight based upon the total weight of the sulfonated alkylbenzene component. In another form of the invention, an alkylbenzene sulfonate component may contain sulfonated 2-phenyl alkylbenzenes in an amount of at least 40.00% by weight based upon the total weight of the sulfonated phenyl alkylbenzene component. In yet another form of the invention, an alkylbenzene sulfonate component may contain sulfonated 2-phenyl alkylbenzenes in an amount of at least 50.00% by weight based upon the total weight of the sulfonated phenyl alkylbenzene component. In yet another form of the invention, an alkylbenzene sulfonate component may contain sulfonated 2-phenyl alkylbenzenes in an amount of at least 60.00% by weight based upon the total weight of the sulfonated phenyl alkylbenzene component. In yet another form of the invention, an alkylbenzene sulfonate component may contain sulfonated 2-phenyl alkylbenzenes in an amount of at least 70.00% by weight based upon the total weight of the sulfonated phenyl alkylbenzene component. In yet another form of the invention, an alkylbenzene sulfonate component may contain sulfonated 2-phenyl alkylbenzenes in an amount of at least 80.00% by weight based upon the total weight of the sulfonated phenyl alkylbenzene component.

By admixture with conventional mixtures of sulfonated linear alkylbenzene detergents, a mixture of sulfonated alkylbenzenes useful as components in detergent formulations having any desired 2-phenyl alkylbenzene isomer content in the range of between about 18.00% and 85.00%, including every hundredth percentage therebetween, may be produced using the materials provided according to the invention. Such mixtures of sulfonated alkylbenzenes are useful as a component in forming detergent and cleaning compositions useful in a wide variety of applications as later illustrated in the examples.

It has also been found that a catalyst according to this invention may be used in combination with an existing aluminum chloride or hydrogen fluoride alkylation facility to afford LAB having a higher 2-phenyl isomer content than would otherwise be available from such plant using conventional catalysts. Thus, an existing facility may be retrofitted to include one or more reactors containing the fluorine-containing mordenite of this invention. In this manner, a slip stream of reactants may be sent to the mordenite with effluent therefrom being introduced back into the conventional alkylation system. This embodiment has several advantages. For example, the cost of capital is minimized since conventional equipment will already be in place. Also, the retrofitted plant can produce higher 2-phenyl isomer LAB at the discretion of its operator, depending on need. That is, the plant need not produce strictly high 2-phenyl isomer LAB and can instead produce high 2-phenyl isomer at its discretion. In one embodiment, a slip stream of reactant is drawn and sent to one or more reactors containing fluorine-containing mordenite catalyst. The effluent from the fluorine-containing mordenite reactor may then be combined with effluent from the HF or aluminum chloride reactor to provide a product having a higher level of 2-phenyl isomer LAB than would otherwise be present in product from an HF or aluminum chloride reactor.

The invention, in one broad respect, is directed at cleaning formulations designed to cleanse a wide variety of surfaces or substrates and which possess increased tolerance to water hardness, wherein the formulations comprise an alkylbenzene sulfonate component having a much higher 2-phenyl isomer content than formulations previously available commercially, and other components known to be useful in formulating soaps, detergents, and the like.

The invention, in another broad respect is a process useful for the production of mono-alkylbenzene, comprising: contacting benzene with an olefin containing from about 8 to about 30 carbons in the presence of fluorine-containing mordenite under conditions such that linear monoalkylbenzene is formed.

In another broad respect, this invention is a process for the production of linear alkylbenzene, comprising: a) contacting benzene and an olefin having about 8 to about 30 carbons in the presence of a fluorine-containing mordenite to form a first linear alkylbenzene stream; b) contacting benzene and an olefin having about 8 to about 30 carbons in the presence of a conventional linear alkylbenzene alkylation catalyst to form a second linear alkylbenzene stream; and c) combining the first linear alkylbenzene stream and the second linear alkylbenzene stream form a third linear alkylbenzene stream, as well as the product made from this process.

In another broad respect, this invention is a process useful for the production of linear alkylbenzene, comprising: combining a product from a conventional linear alkylbenzene alkylation reactor with a product from a linear alkylbenzene alkylation reactor containing fluorine-containing mordenite.

In yet another broad respect, this invention is a process for the production of linear alkylbenzene, comprising: a) dehydrogenating a paraffin to form an olefin; b) sending a primary feed stream of benzene and the olefin through a conduit to a conventional linear alkylbenzene alkylation reactor; c) contacting the primary feed stream in the conventional linear alkylbenzene alkylation reactor with a conventional linear alkylbenzene alkylation catalyst under conditions effective to react the benzene and olefin to form a first linear alkylbenzene product; d) withdrawing a portion of the primary feed stream from the conduit and contacting the portion with a fluorine-containing mordenite under conditions effective to react the benzene and olefin to form a second linear alkylbenzene product; e) combining the first and second linear alkylbenzene products to form a crude linear alkylbenzene stream; and f) distilling the crude linear alkylbenzene stream in a first distillation column to separate benzene that did not react and to form a benzene-free linear alkylbenzene stream.

Such process may optionally include the steps of: g) distilling the benzene-free linear alkylbenzene stream in a second distillation column to separate any olefin and to form a linear alkylbenzene stream; and h) distilling the second olefin free alkylbenzene stream in a third distillation column to provide an overhead of a purified linear alkylbenzene product and removing a bottoms stream containing any heavies.

In another broad respect, this invention is a process useful for the production of monoalkylbenzene, comprising: introducing a feed comprising olefin having about 8 to about 30 carbons and benzene into a fluorine-containing mordenite catalyst bed under conditions such that monoalkylbenzene is produced, allowing benzene, olefin, and mono-alkylbenzene to descend (fall) into a reboiler from the catalyst bed, removing monoalkylbenzene from the reboiler, and heating the contents of the reboiler such that benzene refluxes to further contact the fluorine-containing mordenite.

In yet another broad aspect, this invention relates to mordenite useful for alkylating benzene with olefin having a silica to alumina molar ratio of about 10:1 to about 100:1; wherein the mordenite has been treated with an aqueous hydrogen fluoride solution such that the mordenite contains from about 0.1 to about 4 percent fluorine by weight.

In yet another broad respect, the invention relates to a chemical mixture that contains linear alkylbenzenes produced using the process(es) and/or catalyst(s) taught herein, which chemical mixture is useful for producing a mixture of sulfonated linear alkylbenzenes which mixture contains a higher concentration of sulfonated 2-phenyl alkylbenzenes than previously available using prior art methods and catalysts.

In another broad respect, the invention comprises formulations for finished consumer and industrial strength compositions useful in or as: all-purpose cleaners, pine oil microemulsions, liquid dishwashing soaps, enzyme-based powdered laundry detergents, enzyme-free powdered laundry detergents, and the like, as it has been found that the use of sulfonated LAB mixtures having a higher content of the 2-phenyl isomer with respect to what has been heretofore available from the teachings of the prior art improves the effectiveness and cleaning action of all cleaning compositions which contain conventional sulfonated alkylbenzene detergents, be they linear or branched.

In another broad respect, the invention is a method useful for the preparation of fluorine-containing mordenite, comprising contacting a mordenite having a silica to alumina molar ratio in a range from about 10:1 to about 100:1 with an aqueous hydrogen fluoride solution having a concentration of hydrogen fluoride in the range of from about 0.1 to about 10 percent by weight such that the mordenite containing fluorine is produced, collecting the fluorine-containing mordenite by filtration, and drying.

The fluorine treated mordenite catalyst advantageously produces high selectivities to the 2-phenyl isomer in the preparation of LAB, generally producing selectivities of about 70 percent or more. Also, the fluorine treated mordenite enjoys a long lifetime, preferably experiencing only a 25 percent or less decrease in activity after 400 hours on stream. A process operated in accordance with the apparatus depicted in FIGS. 1 and 2 has the advantage that rising benzene from the reboiler continuously cleans the catalyst to thereby increase lifetime of the catalyst. In addition, this invention advantageously produces only low amounts of dialkylbenzene, which is not particularly as useful for detergent manufacture, as well as only low amounts of tetralin derivatives.

In another aspect the invention provides solid salts of alkylbenzene sulfonates, which solid salts may contain various cations for charge balance.

In another aspect the invention comprises finished detergent compositions useful for cleaning fabrics, dishes, hard surfaces, and other substrates that is formed from components comprising: a) an alkylbenzene sulfonate surfactant component present in any amount between 0.25% and 99.50% by weight based upon the total weight of the finished detergent composition, said component characterized as comprising any amount between 26.00% and 85.00% by weight based upon the total weight of the component, and including every hundredth percentage therebetween, of water-soluble sulfonates of the 2-phenyl isomers of alkylbenzenes described by the general formula:

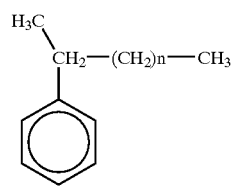

wherein n is equal to any integer between 4 and 16; and b) any amount between 0.50% and 99.75% of other components known to be useful in formulating soaps, detergents, and the like, wherein at least one of said other components is selected from the group consisting of: fatty acids, alkyl sulfates, an ethanolamine, an amine oxide, alkali carbonates, water, ethanol, isopropanol, pine oil, sodium chloride, sodium silicate, polymers, alcohol alkoxylates, zeolites, perborate salts, alkali sulfates, enzymes, hydrotropes, dyes, fragrances, preservatives, brighteners, builders, polyacrylates, essential oils, alkali hydroxides, ether sulfates, alkylphenol ethoxylates, fatty acid amides, alpha olefin sulfonates, paraffin sulfonates, betaines, chelating agents, tallowamine ethoxylates, polyetheramine ethoxylates, ethylene oxide/propylene oxide block copolymers, alcohol ethylene oxide/propylene oxide low foam surfactants, methyl ester sulfonates, alkyl polysaccharides, N-methyl glucamides, alkylated sulfonated diphenyl oxide, and water soluble alkylbenzene sulfonates having a 2-phenyl isomer content of less than 26.00%.

The mordenite catalyst of the present invention is useful as a catalyst in the production of LAB's in accordance with the process of manufacturing LAB's of this invention. LAB is useful as starting material to produce sulfonated LAB, which itself is useful as a surfactant.

Certain terms and phrases have the following meanings as used herein:

"Meq/g" means milliequivalents of titratable acid per gram of catalyst, which is a unit used to describe acidity of the catalysts. Acidity is generally determined by titration with a base, as by adding excessive base, such as sodium hydroxide, to the catalyst and then back titrating the catalyst.

"Conv." and "Conversion" mean the mole percentage of a given reactant converted to product. Generally, olefin conversion is about 95 percent or more in the practice of this invention.

"Sel." and "Selectivity" mean the mole percentage of a particular component in the product. Generally, selectivity to the 2-phenyl isomer is about 70% or more in the practice of this invention.

"Detergent range" means a molecular species which contains an alkyl group that comprises any number of carbon atoms: 8, 9, 10, 11, 12, 13, 14 or 15 per alkyl group, and includes LAB, LAB sulfonates, and mono-olefins.

"Substantially linear" when referring to a hydrocarbon or alkyl chain that is part of an alkylbenzene, whether the alkylbenzene is sulfonated or not, means a hydrocarbon comprising between 7 and 16 carbon atoms linked to one another to form a straight chain, wherein the carbon atoms of said straight chain may have only hydrogen atoms or a methyl group bonded to them as appendages.

"Branched alkyl" when referring to a hydrocarbon or alkyl chain that is part of an alkylbenzene, whether the alkylbenzene is sulfonated or not, means any hydrocarbon comprising between 4 and 18 carbon atoms linked to one another to form a straight chain, wherein one or more of the carbon atoms of said straight chain may have a hydrogen atom and any alkyl group other than a methyl group (including without limitation ethyl, propyl and butyl groups), bonded to them as appendages.

"Branched alkylbenzene" means a molecular species which comprises a branched alkyl chain appended to a benzene ring.

"Branched alkylbenzene sulfonate" means a water-soluble salt of a branched alkylbenzene that has been sulfonated.

"2-phenyl alkylbenzenes" means a benzene ring having at least one alkyl group attached to it, wherein the alkyl group comprises any number of carbon atoms between 7 and 16

(including every integral number therebetween) linked to one another so as to form a substantially linear chain and wherein the benzene ring is attached the alkyl group at a carbon atom that is adjacent to the terminal carbon of the substantially linear chain. Thus, the carbon atom that is attached to the benzene ring has a methyl group and another alkyl group attached to it in a 2-phenyl alkylbenzene.

"Sulfonated 2-phenyl alkylbenzenes" means 2-phenyl alkylbenzenes as defined above which further comprise a sulfonate group attached to the benzene ring of a 2-phenyl alkylbenzene as described above, regardless of the position of the sulfonate group on the ring with respect to the location of the alkyl group; however, it is most common and preferred that the sulfonate group is attached to the benzene ring in the para-position with respect to the alkyl group.

"LAB" means a mixture linear alkylbenzenes which comprises a benzene ring appended to any carbon atom of a substantially linear alkyl chain in the detergent range.

"LAB sulfonates" means LAB which has been sulfonated to include an acidic sulfonate group appended to the benzene rings (thus forming a parent acid), and subsequently rendered to a form more soluble to aqueous solution than the parent acid by neutralization using any of alkali metal hydroxides, alkaline earth hydroxides, ammonium hydroxides, alkylammonium hydroxides, or any chemical agent known by those skilled in the art to react with linear alkylbenzene sulfonic acids to form water-soluble linear alkylbenzene sulfonates.

"2-phenyl isomer" means LAB sulfonates of 2-phenyl alkylbenzenes.

All percentages are expressed in terms of weight percent, unless specified otherwise.

DETAILED DESCRIPTION OF THE INVENTION

Figure 1:
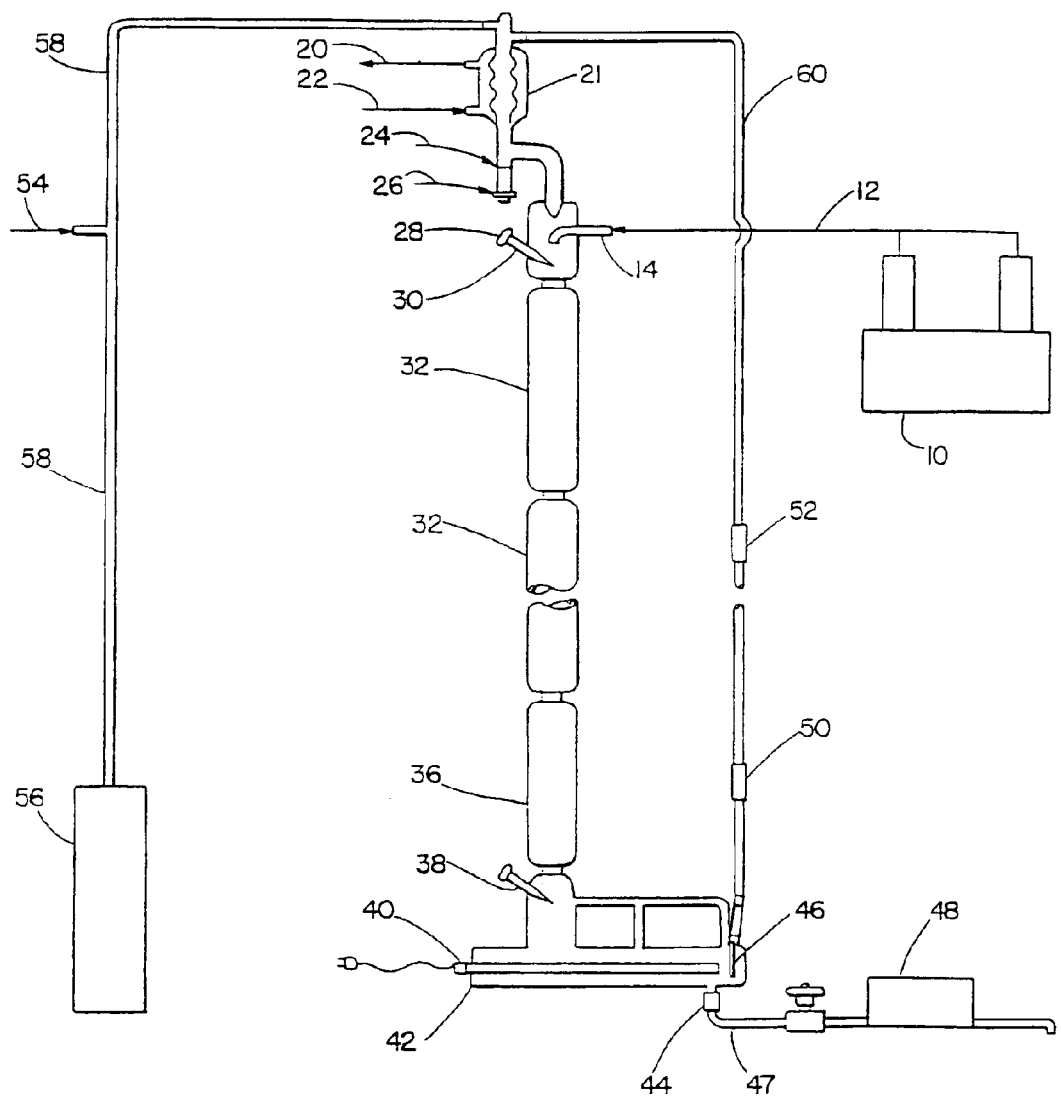
FIG. 1 shows a representation of a first continuous reactive distillation column employed in the practice of this invention.

The catalysts used to prepare the linear alkylbenzenes of this invention is a fluorine-containing mordenite. Mordenite is a type of zeolite. The catalyst of this invention is prepared from hydrogen mordenite (typically having 0.1 percent or less of sodium) having a silica-alumina molar ratio of from about 10:1 to about 100:1. More typically, the starting mordenite has a silica/alumina molar ratio of from about 10:1 to about 50:1. The starting hydrogen mordenite, which is commonly available commercially, is treated with an aqueous solution of hydrogen fluoride ("HF") to produce the active, long-life and highly selective catalyst of the invention. In the course of such HF treatment, as well as during subsequent calcination of said HF-treated mordenite, the silica/alumina molar ratio typically increases. The finished catalysts of this invention show a fluorine content of from about 0.1 to about 4 percent by weight, more typically about 1 percent.

The aqueous solution used to treat the mordenite may contain a range of HF concentrations. Generally, the HF concentration is a minimum of about 0.1 percent by weight. Below such minimum concentration, the effect of the fluorine treatment significantly decreases, resulting in the undesirable need for repeated treatments. Generally, the HF concentration on the upper end is about 10 percent by weight or less. Above a concentration of about 10 percent by weight, the HF is so concentrated that it is difficult to prevent HF from destroying the crystallinity of the mordenite, thereby detrimentally affecting its efficacy as a catalyst for LAB production.

The aqueous HF solution may be prepared by diluting commercially available 48% HF solutions to the desired concentration. Alternatively, HF can be sparged into water to provide an aqueous HF solution.

Typically, the treatment is carried out by adding mordenite powder or pellets to a stirred aqueous HF solution at a temperature of from about 0° C. to about 50° C. The stirring and contacting is continued for a time sufficient to achieve the desired level of fluorine in the mordenite. This time may vary depending on factors such as HF concentration, amount of HF solution relative to the amount of mordenite being treated, speed of agitation is employed, and temperature. After treatment, the mordenite can be recovered by filtration, and then dried. It is also possible to impregnate the mordenite to incipient wetness with a given HF solution, as well as to treat the mordenite with gaseous hydrogen fluoride. Preferably said fluoride-treated mordenite would be calcined in air prior to use in alkylation service. The preferred calcination temperature would be in the range from about 400° C. to about 600° C. Alternative mordenite fluorinating agents to hydrofluoric acid and hydrogen fluoride include ammonium fluoride, fluorided silicon compounds and fluorided hydrocarbons.

The HF-treated mordenite of this invention generally has about 0.1 percent by weight or more of fluorine based on the total weight of the mordenite. Typically, the fluorine-containing mordenite contains about 4 percent by weight or less fluorine. The fluorine-containing mordenite most typically contains about 1 percent by weight of fluorine.

The mordenite can be used in the practice of this invention as a powder, in pellet form, as granules, or as extrudates. The mordenite can be formed into pellets or extrudates using binders well known to those of skill in the art, such as alumina, silica or mixtures thereof.

Reactants for LAB Production

In the practice of this invention, benzene is alkylated with olefin to form LAB. These reactants can be handled and purified as is generally performed by those of ordinary skill in the art. In this regard, it is preferred that the reactants are water and alcohol free The olefins employed in the practice of this invention have from about 8 to about 30 carbons, preferably from about 10 to about 14 carbons, such as is available commercially or produced as dehydrogenated paraffin feed stocks. It is preferred that the olefin be monounsaturated. It is most preferred that the olefin be an alpha-olefin containing a terminal ethylenic unit.

Olefins in the 10 to 14 carbon number range are typically available from the dehydrogenation of a $C_{10}$ to $C_{14}$ paraffin mixture using methods known to those skilled in the art. Dehydrogenation of such paraffins provides a mixture of mono-olefins having a double bond at the terminal carbon in the chain and its neighboring carbon atom, and leaves some of the paraffins unconverted. Thus, the effluent of a dehydrogenation reactor into which was fed a $C_{10}$ to $C_{14}$ mixture typically comprises a mixture which is predominantly paraffins and has an olefin content of about 5 to 20%, and is readily available. Often, the olefin content of said olefin-paraffin mixture may be 8 to 10 weight %.

The process of this invention for producing the 2-phenyl isomer of the LAB having the formula previously set forth above can be carried out using the continuous reactive distillation column depicted in FIG. 1. In FIG. 1, a feed mixture of benzene and olefin, generally at a benzene-to-olefin molar ratio range of about 1:1 to 100:1 flows from feed pump 10 to feed inlet 14 via line 12. The feed mixture falls to packed mordenite catalyst bed 32 where alkylation in the presence of the fluorine-containing mordenite occurs. Alternatively, while not depicted in FIG. 1, the benzene and olefin can be introduced separately into the bed with mixing occurring in the bed, or the reactants can be mixed via an in-line mixer prior to introducing the reactants into the catalyst bed, or the reactants can be injected separately above the bed with mixing affected by use of standard packing above the bed, or the reactants can be sparged into the chamber above the bed. The catalyst bed 32 depicted in FIG. 1 for laboratory scale may be made of two lengths of 1.1 inch internal diameter tubing, the lengths being 9.5 inches and 22 inches. In the catalyst bed 32, the falling feed mixture also contacts rising vapors of unreacted benzene which has been heated to reflux in reboiler 42 by heater 40. Such rising vapors pass over thermocouple 38 which monitors temperature to provide feedback to heater 40. The rising vapors of benzene and/or olefin also pass through standard packing 36 (e.g., 7.5 inches of goodloe packing). The rising vapors heat thermocouple 30 which connects to bottoms temperature controller 28 which activates heater 40 when temperature drops below a set level.

Prior to startup, the system may be flushed with nitrogen which enters via line 54 and which flows through line 58. After startup, a nitrogen blanket is maintained over the system. Also prior to startup and during nitrogen flush, it may be desirable to heat catalyst bed 32 so as to drive off water from the fluorine-containing mordenite.

Residual water from the feed mixture or which otherwise enters the system is collected in water trap 24 upon being liquefied at condenser 21 (along with benzene vapor). If the feed is very dry (free of water) the water trap 24 may not be needed. Removing water leads to longer catalyst lifetime. Hence, the water trap 24 is optional. The same applies to FIG. 2. Condenser 21 is cooled via coolant such as water entering condenser 21 via port 22 and exiting via port 20. As needed, water in water trap 24 may be drained by opening drain valve 26.

As needed, when LAB content in reboiler 42 rises to a desired level, the bottoms LAB product may be removed from the system via line 47, using either gravity or bottoms pump 48 to withdraw the product. When product is so withdrawn, valve 44 is opened.

In FIG. 1, dip tube 46, which is optional, is employed to slightly increase the pressure in reboiler 42 to thereby raise the boiling point of benzene a degree or two. Likewise, a pressure generator 56 may be optionally employed to raise the pressure of the system. Other standard pressure increasing devices can be employed. Pressure can thus be increased in the system such that the boiling point of benzene increases up to about 200° C.

In FIG. 1, control mechanisms for heat shutoff 50 and pump shutoff 52 are depicted which serve to shut off heat and pump if the liquids level in the system rises to such levels. These control mechanisms are optional and may be included so that the catalyst bed does not come into contact with the bottoms of the reboiler. Line 60 connects pump shutoff 52 to the system above condenser 21.

Figure 2:
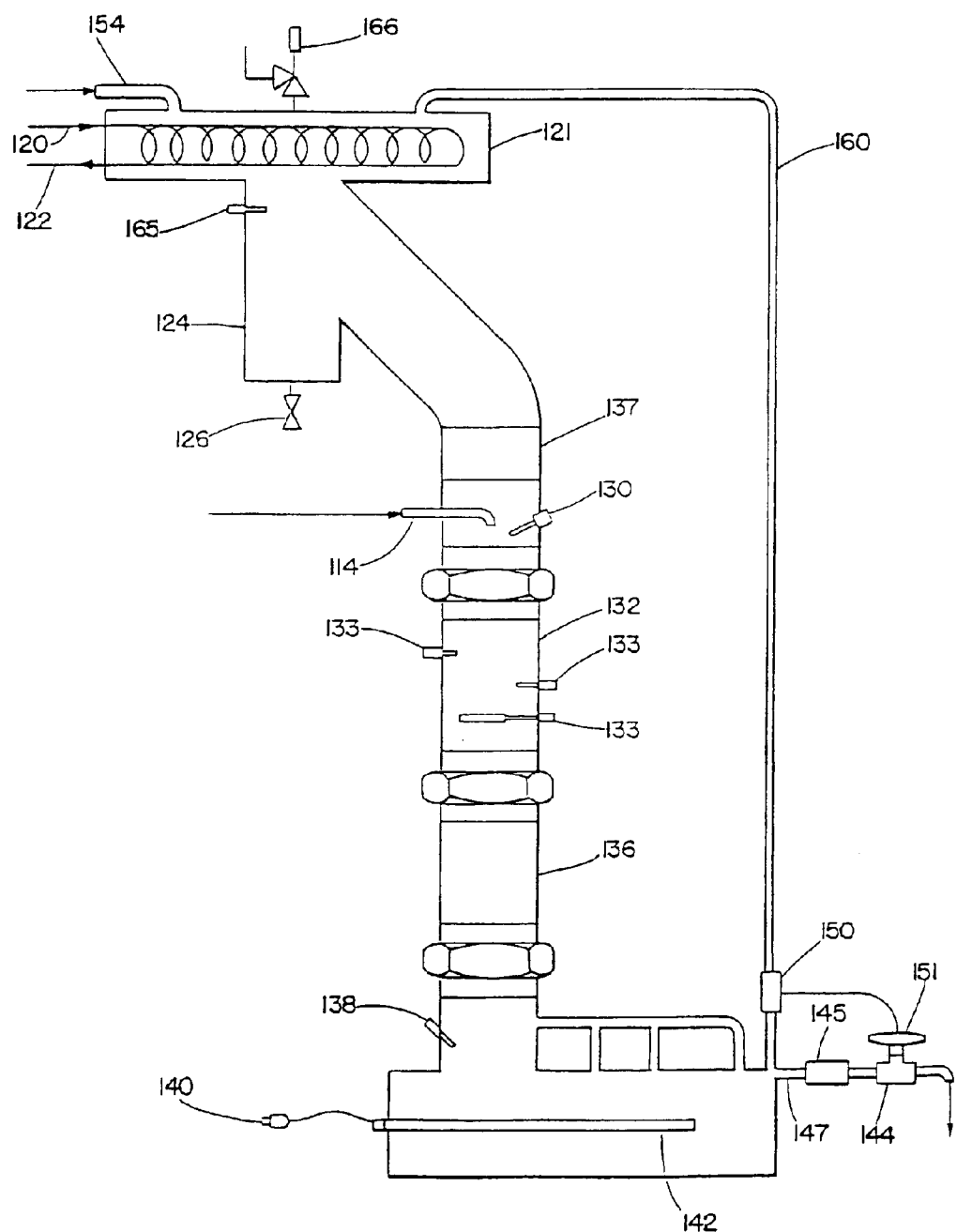
FIG. 2 shows a representation of a second continuous reactive distillation column employed in the practice of this invention.

In the practice of this invention in the alkylation of benzene, a wide variety of process conditions can be employed. In this regard, the temperature in the catalyst bed may vary depending on reactants, rate of introduction into the catalyst bed, size of the bed, and so forth. Generally, the bed is maintained at the reflux temperature of benzene depending on pressure. Typically, the temperature of the catalyst bed is above about 70° C., and most likely about 78° C. or more in order to have reasonable reaction rates, and about 200° C. or less to avoid degradation of reactants and products and to avoid deactivation of the catalyst by coke build-up. Preferably, the temperature is in the range from about 80° C. to about 140° C. The process may be operated at a variety of pressures during the contacting step, with pressures of about atmospheric most typically being employed. When the process is operated using a system as depicted in FIGS. 1 and 2, the reboiler temperature is maintained such that benzene and olefin vaporize, the temperature varying depending on olefin, and generally being from about 80° C. to about 250° C. for olefins having 10 to 14 carbons. The composition of the reboiler will vary over time, but is generally set initially to have a benzene olefin ratio of about 5:1, with this ratio being maintained during the practice of this invention. The rate of introduction of feed into the catalyst bed may vary, and is generally at a liquid hourly space velocity ("LHSV") of about 0.05 $hr^{-1}$ to about 10 $hr^{-1}$, more typically from about 0.05 $hr^{-1}$ to about 1 $hr^{-1}$ benzene to olefin introduced into the catalyst bed is generally from about 1:1 to about 100:1. In commercial benzene alkylation operations, it is common to run at mole ratios of from about 2:1 to about 20:1, which can suitably be employed in the practice of this invention, and to charge said olefins as an olefin-paraffin mixture comprising 5% to 20% olefin content. Said olefin-paraffin mixtures are normally generated commercially through dehydrogenation of the corresponding paraffin starting material over a noble metal catalyst.

Another continuous reactive distillation apparatus is depicted in FIG. 2. In FIG. 2, the feed mixture enters the reactor via feed inlet 114. The feed mixture falls through the column into catalyst bed 132, wherein alkylation to form LAB occurs. A thermowell 133 monitors the temperature of said catalyst bed 132. The catalyst bed 132 may be optionally heated externally and is contained within 1¼ inch stainless steel tubing. Goodloe packing is positioned at packing 136 and 137. LAB product, as well as unreacted benzene and olefin, fall through packing 136 into reboiler 142. In reboiler 142, electric heater 140 heats the contents of reboiler 142 such that heated vapors of benzene and olefin rise from the reboiler 142 to at least reach catalyst bed 132. As needed, the bottoms LAB product may be removed from reboiler 142 by opening bottoms valve 144 after passing through line 147 and filter 145. Residual water from the feed mixture, or which otherwise enters the system, may be condensed at condenser 121 which is cooled with coolant via outlet line 122 and inlet line 120. The condensed water falls to water trap 124, which can be drained as needed by opening drain valve 126. Temperature in the system is monitored via thermocouples 138, 130, and 165. The system includes pressure release valve 166. A nitrogen blanket over the system is maintained by introduction of nitrogen gas via inlet line 154. Level control activator 150 activates bottoms level control valve 151 to open when the liquids level in the reboiler rises to the level control activator 150. Line 160 connects level control activator 150 to the system above condenser 121.

While the systems depicted in FIGS. 1 and 2 show single catalyst bed systems, it may be appreciated that multi-catalyst bed reactors are within the scope of this invention, as well as multiple ports for inlet feeds, water traps, product removal lines, and so forth. Moreover, the process may be run in batch mode, or in other continuous processes using plugflow designs, trickle bed designs, and fluidized bed designs.

It is believed that as average molecular weight of olefins increases, particularly when the average number of carbons exceed 14, the selectivity and conversion to LAB, especially LAB with the 2-isomer, may incrementally decrease. If desired, the product of the alkylation using HF-treated mordenite may be sent to a second, finishing catalyst bed to improve yield. This procedure is optional and is believed to be dependent on the needs and desires of the end user. An example of such a second catalyst is HF-treated clay such as montmorillonite clay having about 0.5% fluoride. Such a catalyst may also serve to lower the bromine number below about 0.1, depending on conditions.

Variable 2-phenyl Isomer Content of Product Using the Mordenite of the Invention in Combination with Conventional LAB Alkylation The fluorine-containing mordenite of this invention generally produces LAB having high 2-phenyl isomer content, such as higher than about 70%. Currently, LAB purchasers who make detergents would prefer to use LAB having a 2-phenyl isomer content in the range from about 30 to about 40 percent, but this level is not available in the marketplace. Conventional LAB alkylation technology do not achieve these higher 2-phenyl isomer levels. HF, which is currently the most widely used catalyst for production of LAB on a commercial scale, produces about 16–18 percent of the 2-phenyl isomer in the product stream from the reactor. Aluminum chloride, in contrast, produces about 26–28 percent of the 2-phenyl isomer. The present inventors recognized that a need exists for a process which produces a 2-phenyl isomer product in the desired range.

It has now been found that the mordenite of this invention can be used in combination with conventional LAB alkylation catalysts, such as HF and aluminum chloride alkylation catalysts. This may be affected by withdrawing a slip stream of reactant that is being sent to the conventional LAB reactor, and directing the slip stream to the mordenite reactor. Since conventional LAB catalysts produce product having a 2-phenyl isomer content much less than that from mordenite of this invention, combining the products from each catalyst results in a product having a higher 2-phenyl isomer content than that from the conventional LAB alkylation catalyst. For example, while the catalyst of this invention typically produces a 2-phenyl isomer content of 70% or more, a typical HF process produces about 16–18% of the 2-phenyl isomer. By combining effluent from each catalyst at given proportions, the resulting mixture will have any desired 2-phenyl isomer content in the range between the 2-phenyl isomer contents of the HF catalyst product and the mordenite catalyst product. Thus, the levels of 2-phenyl isomer may be adjusted by the amount of reactants sent to the mordenite catalyst and/or by storing 2-phenyl isomer product from the mordenite catalyst for later mixing with the product of from the conventional LAB alkylation catalyst to thereby achieve any desired level of 2-phenyl isomer content in the final product. An advantage of this invention pertains to the ability to retrofit an existing, conventional LAB system with a reactor containing fluorine-treated mordenite of this invention. This enables existing users of the conventional LAB technology to augment their existing facilities without interrupting their production. This provides a considerable cost advantage to the producer.

The conventional LAB catalysts used most frequently are HF alkylation reactors and aluminum chloride alkylation catalysts. Other alkylation catalysts include various zeolites, alumina-silica, various clays, as well as other catalysts.

Figure 3:
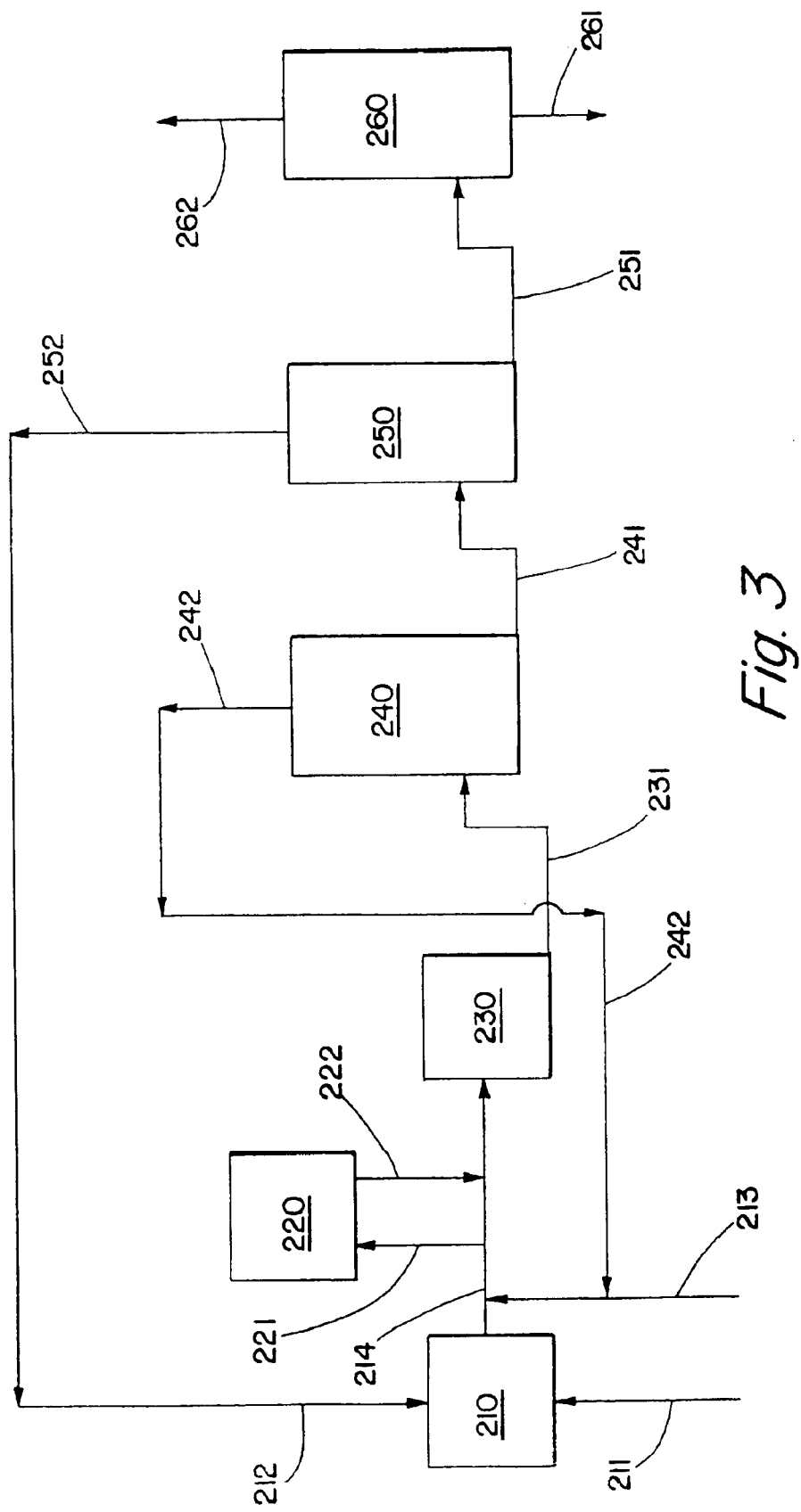
FIG. 3 shows a representative process scheme for one embodiment of this invention where a conventional LAB alkylation reactor is shown in combination with a fluorine-containing mordenite reactor of this invention wherein a slip stream of reactant to the conventional reactor is sent to the mordenite reactor and wherein the flow of high 2-phenyl isomer LAB from the mordenite reactor may be adjusted to vary the 2-phenyl isomer LAB content of the effluent from the conventional LAB alkylation reactor.

FIG. 3 depicts a representative, non-limiting scheme for practice of this invention wherein the fluorine-treated mordenite is used in combination with a HF alkylation reactor to afford LAB having high 2-phenyl isomer contents relative to that produced from the HF reactor alone. The scheme of FIG. 3 is shown in the context of LAB alkylation based on a feed from a paraffin dehydrogenation facility. Prior to this invention, the plant depicted in FIG. 3 would be operated conventionally without use of mordenite reactor 220.

Thus, in conventional operation, fresh paraffin is fed to conventional dehydrogenation apparatus 210 via line 211, with recycled paraffin being introduced from the paraffin column 250 via line 252. Dehydrogenated paraffin from the dehydrogenation apparatus 210 is then pumped into a conventional alkylation reactor 230 containing conventional LAB catalyst, such as HF, via conduit 214. The dehydrogenated paraffin feed may of course be supplied from any provider. The source of dehydrogenated paraffin (olefin) is not critical to the practice of this invention. LAB product from alkylation unit 230 may thereafter be purified by a series of distillation towers.

In this regard, alkylation effluent is delivered to a benzene column 240 by way of line 231. It should be appreciated that the alkylation product may be sent offsite for purification. Further, the particular purification scheme used is not critical to the practice of this invention, but is depicted in FIG. 3 as representative of a typical commercial operation. In FIG. 3, unreacted benzene is distilled off from the crude LAB product. Benzene is then recycled to the alkylation reactor 230. The benzene-free LAB crude product from the benzene column 240 is pumped through line 241 to paraffin column 250 where any paraffin present is distilled off, with the distilled paraffin being recycled to paraffin dehydrogenation unit 210 via line 252. Paraffin-free crude LAB alkylate from the paraffin column 250 is transported to a refining column 260 where purified LAB is distilled and removed via line 262. Heavies (e.g., dialkylates and olefin derivatives) are withdrawn from refining column 260 via conduit 261.

In the practice of this invention, a fluorine-treated mordenite containing reactor 220 is used in conjunction with the conventional alkylation reactor 230. In the embodiment of this invention depicted in FIG. 3, a slip stream of benzene/dehydrogenated paraffin feed is taken from line 214 and pumped through mordenite reactor 220 where high 2-phenyl isomer production is achieved. LAB product from reactor 220, high in 2-phenyl isomer, is then introduced back into line 214 via line 222. Alternatively mordenite reactor 220 may be fed benzene and dehydrogenated paraffin (olefin) directly, rather than by way of a slip stream from line 221. In addition, effluent from reactor 220 may, in the alternative if no unreacted olefin is present, be sent directly to benzene column 240, for later combination with conventional alkylation reactor 230 product or transported and tied into conduit 231, which feeds benzene column 240. It should be appreciated that columns 240, 250, and 260 may be maintained at conditions (e.g., pressure and temperature) well known to those of skill in the art and may be packed with conventional materials if desired.

Figure 4:
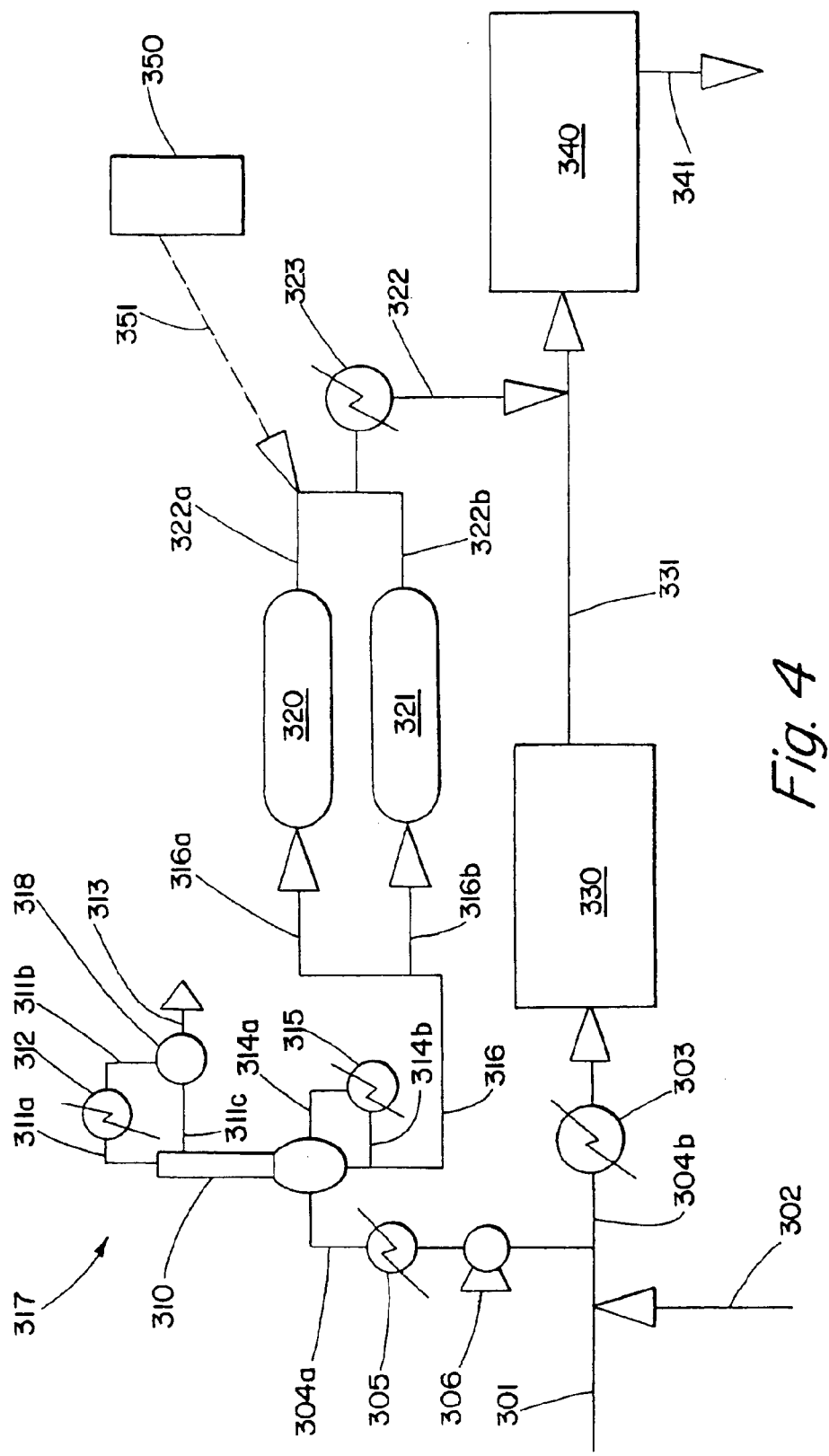
FIG. 4 shows a representative process scheme for an embodiment of this invention where a first conventional LAB alkylation reactor is shown in combination with a fluorine-containing mordenite reactor of this invention wherein a slip stream of reactant to the conventional reactor is sent to one or both of a pair of mordenite reactors and wherein the effluent from the first LAB alkylation reactor and the effluent from the one or both mordenite reactors are combined and flowed into a second conventional LAB reactor.

FIG. 4 depicts an alternative configuration to that shown in FIG. 3. In FIG. 4, dual mordenite beds 320, 321 are used in conjunction with conventional alkylation reactors 330, 340. Conveniently, one of the mordenite reactors may be in operation while the other reactor is down for catalyst regeneration. For example, during operation, olefin feed (dehydrogenated paraffin) is supplied via line 301, with benzene or other aromatic feed stock being provided via line 302. The admixed reactants may flow to standard alkylation reactor 330 via line 304b after passing through heat exchanger 303. A portion of the mixed stream may be withdrawn via line 304a for supply to the mordenite reactor. The extent of the mixed feed stream being withdrawn may be varied depending on the desired level of 2-phenyl isomer in the final product. In another embodiment, the product from the reactor containing mordenite 320, 321 may be fed to the first alkylation reactor 330, particularly if the second alkylation reactor 34 is not employed in the process.

The slip stream reactants may optionally be sent to dewatering unit 317 by application of pump 306 after passing through heat exchanger 305. In the dewatering unit 317, water is distilled from the reactants in dewatering tower 310. Rising vapor exits via line 311a and passes through heat exchanger 312 wherein condensation occurs. Effluent from heat exchanger 312 is advanced to water trap 318 via line 311b. Water is removed from water trap 318 via line 313, with the bottom organic layer being returned to the dewatering tower 310. Dewatered reactants may be removed via line 316 and conveyed to either line 316a or line 316b. Some of the dewatered reactant may be withdrawn by conduit 314b, sent through heat exchanger 315 and returned to the tower 310 via line 314a. In this regard, heat exchanger 315 may serve as a reboiler.

After reaction in either reactor 320 or 321, LAB product is sent to lines 322 and 331 from either line 322a or 322b after passing through heat exchanger 323. When desired, one of the catalyst beds may be regenerated, as by calcination for example, through use of regeneration heater 350, which may be connected to the reactor of choice by dotted line 351 through valving and hardware that are not shown. The reactors 320 and 321 may optionally be run simultaneously. The reactors 320 and 321 may be loaded with mordenite catalyst in any fashion, as would be apparent to one of skill in the art. Typically, a plugged flow arrangement is used. The amount of catalyst employed may vary depending on a variety of considerations such as type and flow rate of reactants, temperature and other variables. The combined effluents from conventional reactor 330 and mordenite reactors 320 or 321 may be fed to a second conventional reactor 340, or optionally may be sent to a purification section directly if no unreacted olefin is present (the conventional reactor serves to complete reaction of any olefin that is not converted in the mordenite reactors 320, 321). In FIG. 4, effluent from the second conventional alkylation reactor is advanced to a purification section. The second alkylation reactor may be used to react unreacted feed stock from reactors 330, 320 and 321 to thereby reduce recycle loads.

It should be appreciated that a wide variety of configurations are contemplated, and the figures should not be construed as limiting this invention or claims hereto. Additional reactors and other equipment may, for example, be used.

The following examples are illustrative of the present invention and are not intended to be construed as limiting the scope of the invention or the claims. Unless otherwise indicated, all percentages are by weight. In the examples, all reactants were commercial grades and used as received. The apparatus depicted in FIG. 1 was employed for examples 2–4. The apparatus depicted in FIG. 1 was used for example 5.

It may be noted that example 2 illustrates LAB production from paraffin dehydrogenate using the fluoride-treated mordenite catalyst of example B, where good catalyst life (250+ hrs) is achieved without catalyst regeneration, while maintaining a 2-phenyl isomer selectivity of >70% and high LAB productivity without significant loss of fluoride. Comparative example 1, on the other hand, using untreated mordenite, with no fluoride added, shows a rapid decline in LAB production. In addition, examples 3 and 4 illustrate LAB production using a 5:1 molar benzene/$C_{10}$–$C_{14}$ olefin feed mix and the fluoride-treated mordenite catalysts of Example B when operating at different LHSV's in the range of 0.2–0.4 $hr^{-1}$. Catalyst life may exceed 500 hours. Example 5 illustrates LAB production with the fluoride-treated mordenite catalyst where the alkylation is conducted at higher temperatures and under pressure. Examples 6–8 illustrate the performance of three HF-treated mordenite catalysts with different fluoride loadings. Example 9 shows how virtually no alkylation activity is observed with a highly-fluorinated mordenite.

EXAMPLE A

This example illustrates the preparation of a hydrogen fluoride-modified mordenite.

To 30 g of acidified mordenite (LZM-8, $SiO_2/Al_2O_3$ ratio 17; $Na_2O$ wt % 0.02, surface area 517 $m^2$/g, powder, from Union Carbide Corp.) was added 600 ml of 0.4% hydrofluoric acid solution, at room temperature. After 5 hours the solid zeolite was removed by filtration, washed with distilled water, dried at 120° C. overnight, and calcined at 538° C.

EXAMPLE B

The example illustrates the preparation of a hydrogen fluoride-modified mordenite.

To 500 g of acidified, dealuminized, mordenite (CBV-20A from PQ Corp.; $SiO_2/Al_2O_3$ molar ratio 20; $Na_2O$, 0.02 wt %; surface area 550 $m^2$/g, 1/16" diameter extrudates, that had been calcined at 538° C., overnight) was added a solution of 33 ml of 48% HF solution in 1633 ml of distilled water, the mix was cooled in ice, stirred on a rotary evaporator overnight, then filtered to recover the extruded solids. The extrudates were further washed with distilled water, dried in vacuo at 100° C., and then calcined at 538° C., overnight.

Analyses of the treated mordenite showed:

F: 1.2%; Acidity: 0.49 meq/g

EXAMPLE 1

This example illustrates the preparation of linear alkylbenzenes using a hydrogen fluoride-modified mordenite catalyst.

To a 500 ml flask, fitted with condenser and Dean Stark Trap was added 100 ml of benzene (reagent grade) plus 10 g of hydrogen fluoride-modified mordenite zeolite, prepared by the method of Example A. The mix was refluxed for 15–20 minutes to remove small amounts of moisture, then a combination of benzene (50 ml) plus 1-dodecene (10 g) was injected into the flask and the solution allowed to reflux for 3 hours.

Upon cooling, the modified mordenite catalyst was removed by filtration, the filtrate liquid flashed to remove unreacted benzene, and the bottoms liquid analyzed by gas chromatography.

Typical analytical data are summarized in Table 1.

TABLE 1

| DODECENE CONV. (%) | LAB ISOMER DISTRIBUTION (%) | | | | | HEAV-IES (%) | LINEAR LAB (LLAB)(%) |
|---|---|---|---|---|---|---|---|
| | 2-Ph | 3-Ph | 4-Ph | 5-Ph | 6-Ph | | |
| 99.7 | 79.9 | 16.6 | 0.8 | 1.3 | 1.3 | 0.2 | 95.9 |

EXAMPLE 2

This example illustrates the preparation of linear alkylbenzenes from paraffin dehydrogenate using a hydrogen fluoride-treated mordenite catalyst.

In example 2, benzene was alkylated with a sample of $C_{10}$–$C_{14}$ paraffin dehydrogenate containing about 8.5% $C_{10}$–$C_{14}$ olefins. Alkylation was conducted in a process unit as shown in FIG. 1.

Alkylation was conducted by first charging 500 ml of a benzene/paraffin dehydrogenate mix (10:1 molar ratio, benzene/$C_{10}$–$C_{14}$ olefin) to the reboiler and 250 cc of the HF-treated mordenite of example B to the 1.1" i.d. reaction zone. The mordenite was held in place using Goodloe packing. The reboiler liquid was then heated to reflux and a benzene plus $C_{10}$–$C_{14}$ paraffin dehydrogenate mix (10:1 molar ratio, benzene/$C_{10}$–$C_{14}$ olefin) continuously introduced into the unit above the catalyst column at the rate of 100 cc/hr. (LHSV=0.4 hr$^{-1}$).

Under steady state, reflux, conditions liquid product was continuously withdrawn from the reboiler and water continuously taken off from the water trap. The crude liquid product was periodically analyzed by gas chromatography. The reboiler temperature was typically in the controlled range of 97–122° C. The column head temperature variability was 78–83° C. A summary of the analytical results may be found in Table 2.

After 253 hours on stream, the recovered HF-treated mordenite catalyst showed by analysis: F: 1.1%; Acidity: 0.29 meq/g; $H_2O$: 0.3%

TABLE 2

| Time on Stream (Hrs) | Sample | Alkylate Conc. (%) | 2-Phenyl Sel. (%) | $C_6H_6$ Conc. (%) |
|---|---|---|---|---|
| 0 | 0 | 1.4 | | 32.3 |
| 2 | 1 | 3.4 | | 19.7 |
| 4 | 2 | 5.8 | 74.9 | 16.6 |
| 6 | 3 | 6.6 | 75.8 | 25.2 |
| 32 | 4 | 7.9 | 80.7 | 27.0 |
| 56 | 5 | 7.8 | 82.7 | 27.0 |
| 69 | 6 | 7.3 | 81.4 | 27.4 |
| 94 | 7 | 6.5 | 82.0 | 27.8 |
| 118 | 8 | 6.0 | 78.4 | 27.7 |
| 142 | 9 | 5.9 | 81.3 | 26.9 |
| 166 | 10 | 5.4 | 81.5 | 27.3 |
| 207 | 11 | 5.3 | 81.3 | 26.1 |
| 229 | 12 | 5.1 | 81.1 | 27.4 |
| 253 | 13 | 4.9 | 81.4 | 28.1 |

COMPARATIVE EXAMPLE 1

This example illustrates the preparation of linear alkylbenzene from paraffin dehydrogenate using an untreated mordenite catalyst. Following the procedures of Example 9, the alkylation unit was charged with 250 cc of untreated, calcined, mordenite, (the starting mordenite of Example B), and the liquid feed comprised benzene plus $C_{10}$–$C_{14}$ paraffin dehydrogenate mix in a 10:1 molar ratio of benzene/$C_{10}$–$C_{14}$ olefin.

Typical results are summarized in Table 3.

The recovered mordenite showed by analysis: Acidity: 0.29 meq/g; $H_2O$: 2.1%

TABLE 3

| Time on Stream (Hrs) | Sample | Alkylate Conc. (%) | 2-Phenyl sel. (%) | $C_6H_6$ Conc. (%) |
|---|---|---|---|---|
| 0 | 0 | | | 11.2 |
| 2 | 1 | 6.50 | | 9.9 |
| 4 | 2 | 7.16 | 73.2 | 17.1 |
| 6 | 3 | 7.09 | 73.1 | 26.4 |
| 22 | 4 | 8.61 | 73.9 | 26.6 |
| 31 | 5 | 10.49 | 67.4 | 15.8 |
| 46 | 6 | 7.39 | 75.0 | 27.7 |
| 70 | 7 | 6.39 | 75.1 | 28.5 |
| 93 | 8 | 6.08 | 73.6 | 23.0 |
| 144 | 9 | 5.21 | 73.6 | 15.8 |
| 157 | 10 | 4.40 | 73.9 | 26.2 |
| 180 | 11 | 3.06 | 69.6 | 27.1 |
| 204 | 12 | 1.32 | | 19.5 |
| 228 | 13 | 1.32 | | 33.3 |

EXAMPLE 3

This example also illustrates the preparation of linear alkylbenzene from paraffin dehydrogenate using a hydrogen fluoride-treated mordenite catalyst.

Following the procedures of Example 2, the alkylation unit was charged with 250 cc of the HF-treated mordenite of Example B, and the liquid feed comprised a benzene plus $C_{10}$–$C_{14}$ paraffin dehydrogenate mix in a 5:1 molar ratio of benzene/$C_{10}$–$C_{14}$ olefin, the reboiler temperature was typically in the range of 122–188° C., the column head temperature 78–83° C. Typical analytical results are summarized in Table 4.

After 503 hours on stream, the recovered HF-treated mordenite catalyst showed on analyis: F: 1.0%; Acidity: 0.35 meq/g; H$_2$O: 0.1%

TABLE 4

| Time on Stream (Hrs) | Sample | Alkylate Conc. (%) | 2-Phenyl Sel. (%) | C$_6$H$_6$ Conc. (%) | Corrected[a] Alkylate Conc. (%) |
|---|---|---|---|---|---|
| 0 | 0 | 1.0 | | 8.9 | 1.1 |
| 2 | 1 | 3.5 | 61.8 | 0.3 | 3.5 |
| 4 | 2 | 7.1 | 72.1 | 0 | 7.1 |
| 6 | 3 | 6.8 | 76.7 | 7.2 | 7.3 |
| 34 | 4 | 8.4 | 79.7 | 14.3 | 9.8 |
| 71 | 5 | 7.2 | 81.8 | 14.6 | 8.5 |
| 96 | 6 | 6.5 | 80.8 | 15.5 | 7.7 |
| 119 | 7 | 6.3 | 80.6 | 15.1 | 7.4 |
| 643 | 8 | 6.0 | 81.0 | 14.3 | 7.0 |

TABLE 4-continued

| Time on Stream (Hrs) | Sample | Alkylate Conc. (%) | 2-Phenyl Sel. (%) | C$_6$H$_6$ Conc. (%) | Corrected[a] Alkylate Conc. (%) |
|---|---|---|---|---|---|
| 168 | 9 | 5.9 | 80.7 | 14.4 | 6.9 |
| 239 | 10 | 5.0 | 78.2 | 8.8 | 5.5 |
| 263 | 11 | 5.3 | 79.2 | 13.5 | 6.2 |
| 288 | 12 | 5.0 | 79.6 | 16.5 | 6.0 |
| 311 | 13 | 5.4 | 79.4 | 4.1 | 5.6 |
| 335 | 14 | 5.5 | 79.2 | 8.2 | 6.0 |
| 408 | 15 | 4.9 | 79.4 | 13.1 | 5.6 |
| 432 | 16 | 4.7 | 78.8 | 14.4 | 5.5 |
| 456 | 17 | 4.4 | 78.5 | 14.1 | 5.1 |
| 479 | 18[a] | 4.7 | 78.6 | 2.7[b] | 4.8 |
| 488 | 19[b] | 4.9 | 78.5 | 2.4[c] | 5.0 |
| 503 | 20[b] | 5.1 | 78.9 | 0.6[c] | 5.1 |

[a]Corrected for benzene in effluent sample.
[b]Applied pressure 8" H$_2$O
[c]Applied pressure 12" H$_2$O

EXAMPLE 4

This example also illustrates the preparation of linear alkylbenzenes from paraffin dehydrogenate using a hydrogen fluoride-treated mordenite catalyst.

Following the procedures of Example 2, alkylation was conducted in the glassware unit of FIG. 1 complete with catalyst column, reboiler, condenser and controls. To the reaction zone was charged 500 cc of HF-treated mordenite of Example B. The liquid feed comprised a benzene plus C$_{10}$–C$_{14}$ paraffin dehydrogenate mix in a 5:1 molar ratio of benzene/C$_{10}$–C$_{14}$ olefin. The feed rate was 100 cc/hr (LHSV:0.2 hr$^{-1}$).

Under typical steady state, reflux, conditions, with a reboiler temperature range of 131–205° C. and a head temperature of 76–83° C., typical results are summarized in Table 5.

TABLE 5

| Pressure (Inch H$_2$O) | Reboiler Temp. (C.) | Time on Stream (Hrs) | Sample | Alkylate Conc. (%) | 2-Phenyl Sel. (%) | C$_6$H$_6$ Conc. (%) | Corrected[a] Alkylate Conc. (%) |
|---|---|---|---|---|---|---|---|
| 12 | 205 | 2 | 1 | 8.2 | 74.3 | 0.5 | 8.3 |
| | 193 | 4 | 2 | 9.2 | 75.0 | 0.4 | 9.2 |
| | 175 | 6 | 3 | 10.0 | 74.8 | 2.3 | 10.3 |
| | 204 | 21 | 4 | 12.7 | 78.7 | 0.3 | 12.7 |
| | 146 | 44 | 5 | 11.7 | 81.0 | 10.4 | 12.9 |
| | 136 | 68 | 6 | 11.5 | 81.8 | 10.0 | 12.7 |
| | | 2–3 days | C[b] | 11.6 | 81.4 | 9.4 | 12.7 |
| | 136 | 93 | 7 | 11.3 | 82.6 | 10.8 | 12.5 |
| | | 4–5 days | C-1[b] | 11.0 | 81.8 | 11.0 | 12.2 |
| | 142 | 165 | 8 | 10.4 | 83.0 | 11.4 | 11.5 |
| | 142 | 189 | 9 | 10.2 | 83.4 | 10.5 | 11.2 |
| | 146 | 213 | 10 | 9.7 | 80.2 | 11.2 | 10.7 |
| | 139 | 238 | 11 | 9.6 | 83.4 | 11.1 | 10.7 |
| | 143 | 261 | 12 | 9.9 | 81.9 | 11.0 | 11.0 |
| | 133 | 333 | 13 | 9.2 | 83.4 | 11.3 | 10.3 |
| | 138 | 356 | 14 | 8.9 | 83.5 | 11.1 | 9.9 |
| | 138 | 381 | 15 | 8.8 | 83.0 | 11.3 | 9.8 |
| | 131 | 405 | 16 | 8.7 | 82.8 | 11.2 | 9.7 |

[a]Corrected for benzene in effluent sample
[b]Composite product

EXAMPLE 5

This example illustrates the preparation of linear alkylbenzenes from paraffin dehydrogenate using a hydrogen fluoride-treated mordenite catalyst.

Following the procedures of Example 2, alkylation of benzene with C$_{10}$–C$_{14}$ paraffin dehydrogenate was conducted using the stainless-steel unit of FIG. 2, complete with catalyst column, reboiler, condenser, and controls. About 250 cc or HF-treated mordenite of Example B was charged to the column. The liquid feed comprised benzene plus C$_{10}$–C$_{14}$ paraffin dehydrogenate mix in a 10:1 molar ratio of benzene/C$_{10}$–C$_{14}$ olefin. The LHSV varied from 0.2 to 0.4 hr$^{-1}$.

Alkylation was conducted over a range of column and reboiler temperatures and a range of exit pressures. Typical results are summarized in Table 6.

TABLE 6

| Column Temp (° C.) | Pressure DIFF (psi) | Pressure EXIT (psi) | Pot Temp. (° C.) | Time (hr) | Sample (#) | Alkylate Conc. (%) | 2-Phenyl Sel. (%) | $C_6H_6$ Conc. (%) |
|---|---|---|---|---|---|---|---|---|
| 149–129 | 0.1 | 0 | 188 | 4 | 1 | 3.8 |  | 6.3 |
| 152–126 | 0 | 0 | 200 | 20 | 2 | 1.8 |  | 32.7 |
| 195–108 | 0 | 0 | 199 | 25 | 3 | 5.7 |  | 8.7 |
| 218–111 | 0 | 0 | 201 | 28 | 4 | 0.8 |  | 67.5 |
| 212–118 | 0 | 0 | 201 | 44 | 5 | 8.8 | 71.7 | 4.5 |
| 209–114 | 0.2 | 0 | 198 | 52 | 6 | 2.4 |  | 47.3 |
| 228–116 | 0 | 0 | 197 | 68 | 7 | 6.9 | 72.6 | 12.4 |
| 187–107 | 0.5 | 0 | 197 | 76 | 8 | 2.9 | 74.6 | 44.1 |
|  |  |  |  | 76 | 9[a] | 4.8 | 72.9 | 25.3 |
|  |  |  |  |  | 9C[b] | 6.8 | 72.2 | 1.0 |
| 174–107 | 0 | 0 | 178 | 6 | 10 | 4.1 | 79.2 | 54.9 |
| 170–106 | 0 | 0 | 172 | 22 | 11 | 2.0 |  | 59.8 |
|  |  |  |  | 28 | 12[a] | 6.6 | 76.8 | 26.8 |
| 142–107 | 0 | 0 | 136 | 31 | 13 | 4.8 | 67.9 | 18.9 |
| 141–110 | 0 | 0 | 138 | 47 | 14 | 4.4 | 65.9 | 16.9 |
| 142–110 | 0 | 0 | 136 | 55 | 15 | 5.0 | 63.9 | 16.6 |
| 168–111 | 0 | 0 | 131 | 71 | 16 | 4.1 | 64.8 | 16.7 |
| 170–108 | 0 | 0 | 150 | 79 | 17 | 5.0 | 72.0 | 8.8 |
| 175–113 | 0 | 0 | 143 | 95 | 18 | 5.9 | 68.1 | 15.2 |
| 145–106 | 0 | 5.2 | 188 | 14 | 19 | 3.2 | 60.2 | 9.0 |
| 149–108 | 0 | 4.2 | 186 | 20 | 20 | 4.8 | 66.3 | 12.0 |
| 160–118 | 0 | 11.7 | 213 | 29 | 21 | 4.2 |  | 6.7 |
| 160–119 | 0 | 9.3 | 210 | 44 | 22 | 5.2 |  | 6.6 |

[a]Composite product
[b]Stripped composite product

EXAMPLES 6–8

These examples illustrate the preparation of linear alkylbenzene using hydrogen fluoride-modified mordenite catalysts with different fluoride treatment levels.

Following the procedures of Example 1, the alkylation unit was charged with benzene (100 ml), a 10 g sample of hydrogen fluoride-modified mordenite prepared by the procedure of Example B, plus a mix of benzene (50 ml) and 1-decene (10 g). Three HF-treated mordenites were tested, having the composition:

| Catalyst "C" | 0.25% HF on mordenite (CBV-20A) |
| Catalyst "D" | 0.50% HF on mordenite (CBV-20A) |
| Catalyst "E" | 1.0% HF on mordenite (CBV-20A) |

In each experiment samples of the bottoms liquid fraction were withdrawn at regular periods and subject to gas chromatography analyses. The results are summarized in Table 7.

TABLE 7

| CATALYST | TIME | % LLAB | % ISOS | % HVY | % 2Ph | % 3Ph | % 4Ph | % 5Ph | % 6&7Ph |
|---|---|---|---|---|---|---|---|---|---|
| D | 10 | 11.75 | 0.14 | 0 | 73.36 | 21.87 | 2.89 | 0.94 | 1.02 |
|  | 20 | 12.43 | 0.21 | 0 | 72.97 | 21.96 | 3.14 | 1.13 | 0.81 |
|  | 30 | 12.88 | 0.21 | 0 | 72.67 | 22.13 | 3.03 | 1.16 | 1.01 |
|  | 40 | 12.27 | 0.22 | 0 | 73.02 | 21.92 | 2.85 | 1.06 | 1.14 |
|  | 50 | 12.15 | 0.98 | 0 | 72.46 | 21.67 | 3.21 | 1.17 | 1.49 |
|  | 50 | 12.24 | 1.01 | 0 | 72.53 | 21.63 | 3.23 | 1.12 | 1.44 |
|  | 60 | 12.28 | 0.21 | 0 | 72.96 | 22.07 | 2.93 | 1.14 | 0.91 |
|  | 60 | 11.98 | 0.21 | 0 | 72.97 | 22.21 | 2.93 | 1.17 | 0.83 |
| C | 10 | 12.2 | 0.18 | 0 | 72.54 | 22.46 | 3.21 | 0.98 | 0.82 |
|  | 20 | 12.7 | 0.39 | 0 | 71.51 | 22.61 | 2.91 | 1.02 | 2.13 |
|  | 30 | 12.52 | 0.21 | 0 | 71.96 | 22.68 | 2.96 | 1.04 | 1.36 |
|  | 40 | 12.75 | 0.21 | 0 | 71.84 | 22.67 | 3.22 | 1.02 | 1.25 |
|  | 50 | 12.98 | 0.21 | 0 | 71.57 | 22.81 | 3.16 | 1.08 | 1.39 |
|  | 60 | 12.54 | 0.21 | 0 | 71.45 | 22.81 | 3.19 | 1.12 | 1.44 |
|  | 60 | 12.33 | 0.21 | 0 | 71.61 | 22.87 | 2.92 | 1.05 | 1.31 |
| E | 10 | 10.56 | 0.05 | 0 | 75.19 | 19.41 | 2.18 | 3.22 |  |
|  | 20 | 12.95 | 0.15 | 0 | 74.36 | 19.23 | 3.01 | 3.4 |  |
|  | 30 | 13.44 | 0.18 | 0 | 74.11 | 19.42 | 3.2 | 3.27 |  |
|  | 40 | 13.16 | 0.15 | 0 | 074.16 | 19.38 | 3.12 | 3.34 |  |
|  | 50 | 13.1 | 0.15 | 0 | 74.43 | 19.16 | 3.21 | 3.28 |  |
|  | 60 | 12.83 | 0.15 | 0 | 74.28 | 19.49 | 2.88 | 3.35 |  |
|  | 60 | 12.87 | 0.16 | 0 | 73.82 | 19.97 | 2.8 | 3.2 |  |

EXAMPLE 9

This example illustrates the inactivity of a heavily loaded hydrogen-fluoride modified mordenite catalyst.

Following the procedures of Example 2, the alkylation unit was charged with 100 cc of a hydrogen fluoride-treated mordenite (CBV-20A) prepared by the method of Example B but having a much higher loading of HF (fluoride content 4.8%). The acidity of said HF-treated mordenite was 0.15 meq/g.

No significant amount of alkylated product was detected by gas chromatography.

Compositions Having Enhanced Water Hardness Tolerance

A surprising observation of increased water hardness tolerance was unexpectedly observed when using LAB sulfonates having a high 2-phenyl isomer content in various cleaning formulations, as set forth below. As is well-known to those of ordinary skill in the chemical arts, most ordinary "tap" water contains varying amounts of cations of the alkaline earth metals calcium and magnesium. These metals are well known to form relatively insoluble complexes (a.k.a. "soap scum") with most soap and detergent molecules, including the LAB sulfonate materials of the prior art. Such complexation frequently results in precipitation of the salts formed by the union of the above-mentioned cations with materials commonly used as soaps, and such complexation results in precipitation of the complex with an attendant effective decrease of the total concentration of detergent in solution. This is an especially troubling problem in areas such as parts of Texas where the local water supply may contain as much as 0.10% of calcium and magnesium hardness, which render some soaps and detergents essentially useless. To reduce the effects of hardness, formulators must often add a chelating agent such as borax or EDTA or one of its sodium salts, to form stable, soluble complexes with hardness minerals, thus masking and effectively reducing the effective concentration of the hardness minerals.

It has been unexpectedly discovered that ionic metallic species such as alkaline earth metal cations which normally hinder detergent activity by complexation as described above do not form insoluble complexes with the LAB sulfonates having a high 2-phenyl isomer content as provided herein as readily as they do with LAB sulfonates in formulations provided by a prior art. The net result of the reluctance of such ionic metallic species to form insoluble complexes with LAB sulfonates having a high-2-phenyl isomer provided by the invention and the formulations described herein is that an effectively higher concentration of such active detergent components is present in solution and available for solubilization of oils and general cleaning of exposed substrates. This result is astounding, since hardness minerals have forever been an issue in the formulation of every detergent and cleaning composition because of their propensity to form insoluble salts with surface active agents. Thus, the formulations of this invention are pioneering insomuch as they represent a first major step away from considering alkaline earth cations as being an issue in the formulation of detergents and the like.

Through use of the LAB sulfonates having a high 2-phenyl isomer content as provided herein, formulators may in many instances omit a chelating agent from their formulations, or at the least, only moderate, reduced amounts would be required. Since such chelants are relatively costly, a savings in manufacture from the standpoints of blending and raw material quantities may be passed on to the public.

Figure 5:
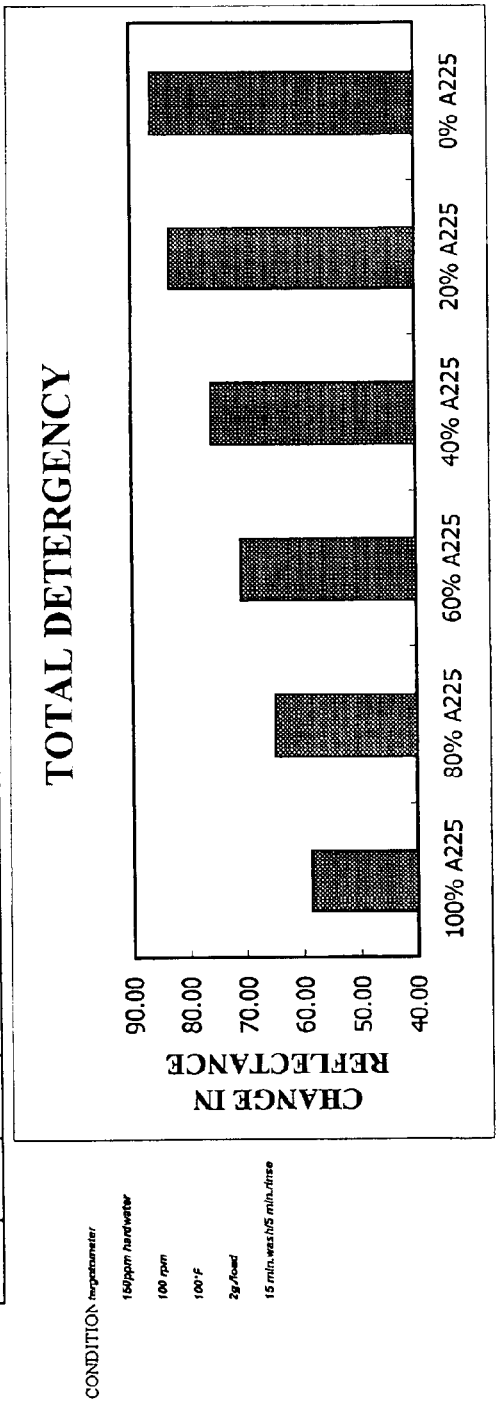
FIG. 5 shows detergency test data on various dirt substances.

Cleaning compositions which utilize an alkylbenzene sulfonate of this invention having a 2-phenyl isomer content of about 80% in the stead of those having a 2-phenyl isomer content of less than about 50% are in general are possessive of much greater cleaning strength. The increase in cleaning performance provided by the linear alkylbenzene sulfonates of this invention having a 2-phenyl isomer content of about 80% ("Super High 2-Phenyl") is illustrated by the data set forth in FIG. 5. In FIG. 5, the total detergency of a blend comprising a conventional linear alkylbenzene sulfonate (denoted as A225 that comprises a 2-phenyl isomer content of about 16% to 18% of the total alkylbenzene sulfonates present; A225 is available from Huntsman Petrochemical Corporation located at 7114 North Lamar Blvd., Austin, Tex.) containing various added amounts of Super High 2-Phenyl is illustrated as performance from laundry testing data. For this series of tests, Super High 2-Phenyl was blended with A225 holding the total amount of actives constant at 10%. The samples were tested in a 6 pot Terg-o-tometer® (US Testing Corporation) at 2 grams per liter of detergent at 100 degrees Fahrenheit, using a 150 ppm hard water with a 15 minute wash cycle followed by a 5 minute rinse. Standardized soil swatches were used to assess the detergency. Results were obtained by measuring the reflectance of the swatches both before and after cleaning using a Hunter Lab Color Quest reflectometer using the L-A-B scale. All swatches were run in triplicate and the results averaged. Soil swatches used were: dirty motor oil, dust sebum, grass stain, blood/milk/ink stain, olive oil (EMPA), clay, and clean white swatches, to measure redeposition. Both cotton and polyester/cotton blends were evaluated for all soils. The results show that the cleaning performance increases with increasing percentage of Super High 2-Phenyl in the blend. The results for the detergent which employed 100% of Super High 2-Phenyl were as much as 50% higher than the conventional-LAS.

Figure 6:
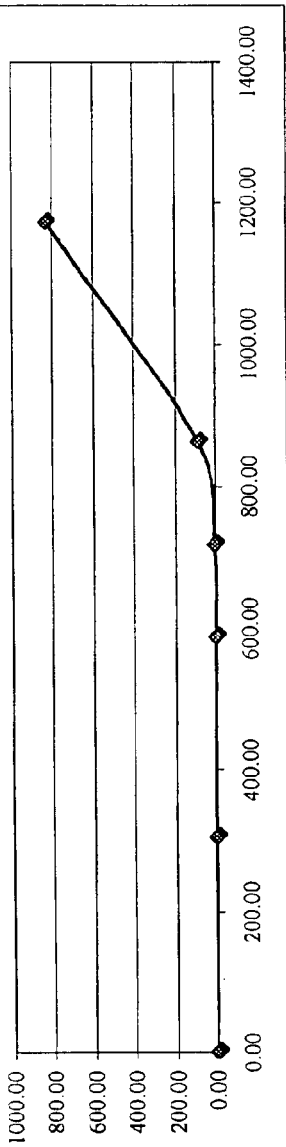
FIG. 6 shows turbidity test data on conventional LAB sulfonate surfactant.

As mentioned above, detergents formulated using Super High 2-Phenyl exhibit an increased tolerance to water hardness with respect to those formulated using conventional, commercially-available linear alkyl benzene sulfonate detergent components. FIG. 6 provides turbidity data to evidence the hardness tolerance of conventional LAS (linear alkyl benzene sulfonate) surfactant A225 present at about 1% aqueous at various levels of water hardness, as measured in NTU units (using a turbidimeter from Orbeco-Helige of Farmingdale, N.Y.), the use of which is well known to those of ordinary skill in the art. In FIG. 6, the point at which the solution turbidity first undergoes a dramatic increase is the point approximately corresponding to the solubility limit of the complex formed by the hardness minerals found in the water used and the detergent component. Thus, formulations which employ conventional linear alkylbenzene sulfonate components similar to A225 begin to experience a decrease in the effective concentration of a main ingredient at a water hardness level of around 750 ppm. Of course such effect will be more pronounced for consumers wishing to ration detergents by using less soap in a given volume of water than the recommended amount, since the amount of total hardness with respect to available sulfonate will be greatly increased which may in some cases bind up more than half of the sulfonate present.

Figure 7:
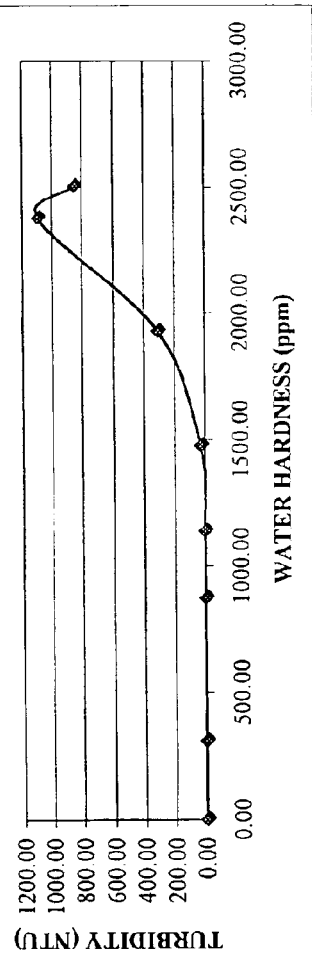
FIG. 7 shows turbidity test data on high 2-isomer LAB sulfonate according to the invention.

FIG. 7 provides data for the same hardness tolerance data as was gathered for FIG. 6 present at about 1% aqueous; however, the LAS used for gathering these data was the Super High 2-Phenyl LAS. From the data in FIG. 7, it is evident that significant amounts of water-insoluble compounds are not formed until a hardness level of about 1500 ppm is reached, which is about twice the hardness tolerance of conventional materials. Since the formulations according to the invention contain high amounts of the 2-phenyl isomer of linear alkylbenzene sulfonates, they not only have increased detergency power, but are also more tolerant to water hardness. Thus, less active chemical may be used in a formulation to give it equal cleaning power to prior art formulations which contain greater amounts of linear alkylbenzene sulfonates. Lowering the amount of active chemical in the formulation saves in raw material costs, blending operations, and transportation costs, which savings may be passed on to the public.

Figure 8:
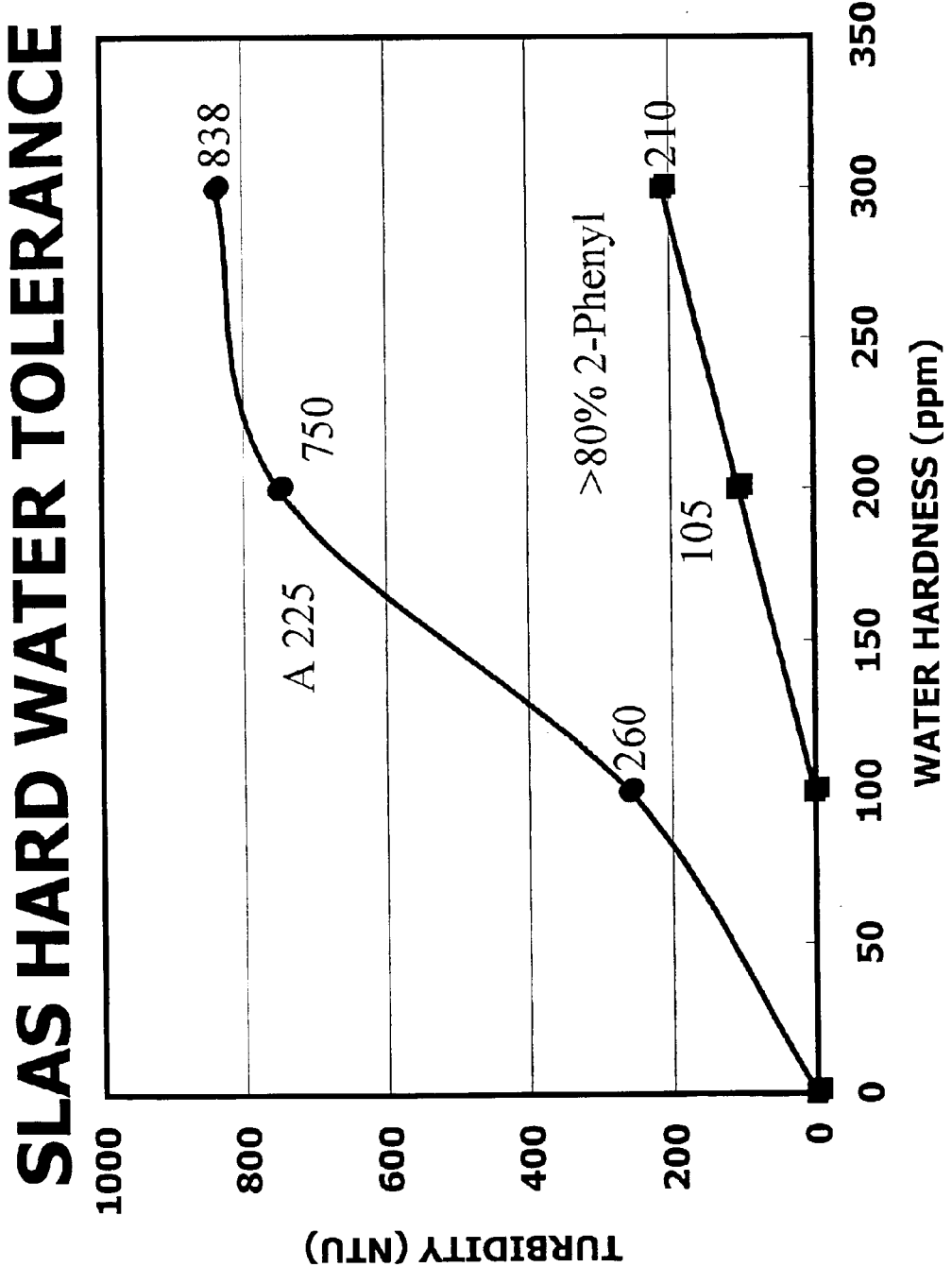
FIG. 8 shows water hardness tolerance test data of high 2-isomer LAB sulfonate according to the invention and conventional LAB sulfonate detergents.

FIG. 8 provides data for the same hardness tolerance data as was gathered for FIGS. 5 and 6; however the surfactant concentration was reduced to about 0.1% aqueous to show the effect of reduced surfactant concentration, since the point at which precipitates begin to form is dependent upon the total amount of surfactant present. In FIG. 8, both A225 and an alkylbenzene sulfonate provided according to the invention having a 2-phenyl isomer are compared. From these data, it is evident that significant amounts of water-insoluble compounds are formed at hardness levels of about 25 ppm using the conventional A225 material while the Super High 2-phenyl material does not show any precipitation until the hardness level of four time this amount or about 100 ppm is achieved.

Since such a large number of formulations of various cleaning compositions contain linear alkylbenzene sulfonates as a main detergent component, the breadth of applicability of the discoveries according to this invention should be readily apparent. Thus, all cleaning compositions known in the prior art which contain sulfonated linear alkylbenzenes can be increased in effectiveness and cleaning strength by being reformulated to replace the sulfonated linear alkylbenzenes currently used with a sulfonated linear alkylbenzene surfactants provided by this invention that have an increased percentage of 2-phenyl alkylbenzene isomers. Further, since it is possible to blend an LAB sulfonate having a high 2-phenyl isomer content produced in accordance with the present invention (on the order of about 85%) with conventional LAB sulfonates, it is also possible according to the invention to provide an LAB sulfonate component useful for forming a detergent composition or cleaning formulation in which the component has a 2-phenyl isomer content of any selected value between about 18% and 85% by weight based upon the total combined weight of all isomers of LAB sulfonate present. As shown in Table 5, alkylbenzenes that contain amounts of the 2-phenyl isomer in excess of 80% may be readily produced according to the instant process using the instant catalyst. As also mentioned, formulators who make finished detergents would prefer to use LAB based surfactants having a 2-phenyl isomer content in the range from about 30 to 40 percent, but this level has not heretofore been available in commercial quantities. Through use of the instant invention, a wide variety of cleaning products comprising LAB sulfonates having between 30% and 40% of 2-phenyl isomer are easily achieved for the first time on a commercial scale. Below are set forth examples of some superior formulations which employ sulfonated linear alkylbenzenes as surfactants. In each example, the LAB sulfonate is a sulfonate such as that produced in accordance with table 2, and having a 2-phenyl isomer content of about 81%. In the examples, the term "LAB sulfonate having 81% 2-phenyl content" means an LAB sulfonate having a 2-phenyl isomer content of 81% based upon the total of all LAB sulfonate isomers present in the LAB sulfonate. In each of the Examples given below, all of the ingredients were combined with one another and mixed until homogeneous. Then, in each case, the final mixtures were adjusted, as is done according to a preferred form of the invention, to a pH in the range of 10–11 using aqueous NaOH and HCl, as needed. However, any final pH level in the range of about 7–12 is may be achieved.

It will be seen in the examples below that there are components in each of the formulas other than the alkylbenzene surfactant component having a high 2-phenyl isomer content. These other components are known by those of ordinary skill in this art to be useful in formulating soaps, cleaning compositions, hard surface cleaners, laundry detergents, and the like. For purposes of this invention and the appended claims, the words "other components known to be useful in formulating soaps, detergents, and the like" means any material which a formulator of ordinary skill in the soap or detergent arts recognizes as adding a benefit to a combination that is intended to be used as a cleaning composition, regardless of the substrate that is intended to be cleansed. Such includes every material that has been known in the prior art to be useful in soap and detergent formulations.

In each of the Examples which follow, all percentages are given on a percent by weight basis based on the total weight of the finished composition, unless noted otherwise.

EXAMPLE 10

All Purpose Cleaner

| | |
|---|---|
| LAB sulfonate having 81% 2-phenyl content | 3.3 |
| alkyl sulfate | 1.6 |
| coconut fatty acid | 1.8 |
| monoethanolamine | 1.5 |
| SURFONIC ® L12-6 | 12.4 |
| Amine oxide | 0.9 |
| Soda ash | 0.7 |
| Water | 77.8 |
| Total | 100 |

EXAMPLE 11

Pine Oil Microemulsion

| | |
|---|---|
| Pine Oil | 20.0 |
| SURFONIC ® L12-8 | 4.7 |
| LAB sulfonate having 81% 2-phenyl content | 7.8 |
| Isopropanol | 11.0 |
| Triethanolamine | 4.7 |
| Water | 51.8 |
| Total | 100 |

EXAMPLE 12

Value Blend Powdered Laundry Detergent

| | |
|---|---|
| LAB sulfonate having 81% 2-phenyl content | 6.5 |
| SURFONIC ® N-95 | 4.3 |
| Soda ash | 29.8 |
| Sodium chloride | 45.7 |

-continued

| | |
|---|---|
| Sodium silicate | 11.6 |
| Polymer | 2.1 |

EXAMPLE 13

Premium Blend Powdered Laundry Detergent

| | |
|---|---|
| LAB sulfonate having 81% 2-phenyl content | 7.1 |
| Sodium alkyl sulfate | 13.3 |
| Alcohol ethoxylate | 2.6 |
| Zeolites | 34.7 |
| Soda ash | 19.6 |
| Sodium silicate | 1.0 |
| Sodium perborate | 0.9 |
| TAED | 0.5 |
| Sodium sulfate | 19.3 |
| Protease enzyme | 0.5 |
| Cellulase enzyme | 0.5 |
| Total | 100 |

EXAMPLE 14

Value Blend Laundry Concentrate

| | |
|---|---|
| LAB sulfonate having 81% 2-phenyl content | 18.5 |
| SURFONIC ® N-95 | 75.00 |
| Monoethanolamine | 6.50 |
| Total | 100 |

EXAMPLE 15

Value Blend Laundry Detergent

| | |
|---|---|
| Concentrate from Example 14 | 7.0000 |
| Water (well) | 92.168 |
| Optical Brightener | 0.0100 |
| Salt | 0.1352 |
| Salt | 0.6148 |
| Preservative | 0.0100 |
| Dye | 0.0020 |
| Fragrance | 0.0600 |
| Total | 100 |

EXAMPLE 16

Value Blend Laundry Concentrate

| | |
|---|---|
| LAB sulfonate having 81% 2-phenyl content | 17.4 |
| SURFONIC ® N-95 | 34.8 |
| SURFONIC ® T-15 | 17.4 |
| POGOL ® 300 | 8.0 |
| Monoethanolamine | 2.4 |
| Water | 20.0 |
| Total | 100 |

EXAMPLE 17

Value Blend Laundry Detergent

| | |
|---|---|
| Concentrate from Example 16 | 50.000 |
| Water | 44.245 |
| Optical brightener A | 0.15 |
| Sodium chloride | 0.500 |
| Polyacrylate A | 2.500 |
| Chelating agent | 1.00 |
| NaOH (50.0% aq.) | 0.220 |
| Fragrance | 0.300 |
| Preservative | 0.080 |
| Melaleuca oil | 0.005 |
| Total | 100 |

EXAMPLE 18

Premium Laundry Detergent Concentrate

| | |
|---|---|
| LAB sulfonate having 81% 2-phenyl content | 18.50 |
| SURFONIC ® N-95 | 75.00 |
| Monoethanolamine | 6.50 |

EXAMPLE 19

Premium Laundry Detergent with Enzymes

| | |
|---|---|
| Concentrate from Example 18 | 30.0000 |
| Water (well) | 56.2632 |
| Optical brightener | 0.0500 |
| Calcium dichloride | 0.1000 |
| Sodium chloride | 0.6148 |
| Preservative | 0.0100 |
| Dye | 0.0020 |
| Fragrance | 0.0600 |
| Propylene glycol | 10.0000 |
| Borax | 2.0000 |
| Protease enzyme | 0.7000 |
| Lipase enzyme | 0.2000 |
| Total | 100 |

EXAMPLE 20

Premium Liquid Dishwashing Formulation I

| | |
|---|---|
| LAB sulfonate having 81% 2-phenyl content | 25.735 |
| De-ionized water | 16.316 |
| Magnesium hydroxide | 1.133 |
| Sodium hydroxide (38% aq.) | 3.591 |
| SURFONIC® SXS-40 (40% aq.) | 15.000 |
| Propylene glycol | 6.000 |
| Sodium lauryl ether sulfate EO 3:1 (70% aq.) | 14.286 (molecular weight = 440) |
| Cocoamidopropyl betaine (38% aq.) | 15.789 |
| Ethanol | 0.0300 |
| Tetrasodium EDTA | 0.1500 |
| Preservative | 0.2000 |
| Dye (0.8% aq.) | 1.0000 |
| Fragrance | 0.5000 |
| Total | 100 |

EXAMPLE 21

Premium Liquid Dishwashing Formulation II

| | |
|---|---|
| LAB sulfonate having 81% 2-phenyl content | 10.200 |
| De-ionized water | 35.567 |
| Magnesium hydroxide | 1.133 |
| Sodium hydroxide (38% aq.) | 1.250 |
| SURFONIC ® SXS-40 (40% aq.) | 15.000 |
| Propylene glycol | 6.000 |
| Sodium lauryl ether sulfate (40% aq.) | 20.000 (molecular weight = 440) |
| Alkyl polyglycoside (50% aq.) | 6.000 |
| Fatty acid MEA amide | 3.000 |
| Tetrasodium EDTA | 0.150 |
| Preservative | 0.200 |
| Fragrance | 0.500 |
| Total | 100 |

The above examples are intended to be exemplary of the versatility of the compositions produced according to the invention with respect to the formulation of household and commercial cleaning formulations, and are not intended to be delimitive thereof in any way whatsoever. Any formulation of a soap, detergent, cleaning composition, whether liquid or solid, regardless of its intended use, that currently contains a LAB sulfonate as a component can be increased in effectiveness by having the current commercial LAB sulfonate component used in its formulation removed and a LAB sulfonate component having an elevated 2-phenyl isomer content substituted therefor. The present invention thus represents a revolutionary advance in the detergent arts, since the preferred 2-phenyl isomer may now be produced in high yield for approximately the same cost as inferior prior art LAB sulfonate mixtures.

It has also been discovered that salts of alkylbenzene sulfonates having a 2-phenyl isomer content greater than about 60% may be isolated as solids at room temperature. This result is surprising since salts of alkylbenzene sulfonates have heretofore been believed to exist only in liquid form. Thus, by the present invention, it is now possible to provide dry powder formulations comprising alkylbenzene sulfonates, such as dry laundry detergents, dry dishwashing detergents, etc. Such dry formulations may be provided using existing blending techniques, including the use of conventional dry processing equipment such as ribbon blenders, etc., and also include detergent tablets for laundry use.

To produce a solid alkylbenzene salt according to a preferred form of the invention, one begins with the sulfonic acid mixture which is produced from sulfonating an alkylbenzene mixture prepared in accordance with the invention, such as any of samples 4 through 7 of table 2 above, which contain more than about 80.0% of the 2-phenyl isomers. Such sulfonic acids are then dissolved in water to a concentration of about 10.0% by weight, and neutralized by slow addition of an alkaline aqueous solution of the desired cation, such as through the use of alkali hydroxides, until stoichiometric neutralization has occurred, which in the case of sodium and potassium is when a pH of about 10.5 is reached. Finally, the water is removed by evaporation or by other means known to those skilled in the chemical arts, such as through the use of a ROTOVAP® evaporator or the like, thus leaving crystals of the alkylbenzene sulfonate salt. Such crystals may be conveniently purified further by recrystallization from ethanol. The sodium salts of alkylbenzene sulfonate according to sample 4 of table 2 have a melting point of about 84 degrees centigrade, and the potassium salts of alkylbenzene sulfonate have a melting point of about 65 degrees centigrade using differential scanning calorimetry according to ASTM specification D-3417.

Cationic surfactants may also function as a cation in forming a stable, solid salt of an alkylbenzene sulfonate. Cationic surfactants are well known in the art as being surfactants with a positively-charged ionic group in their molecular structure, such as the as quaternary ammonium compounds. Cationic surfactants are known to function together with other parts of a formulated detergent system to lower the water's surface tension. They are typically used in wash, rinse and dryer-added fabric softeners. Thus, when a cationic surfactant is employed for providing charge balance in a solid alkylbenzene sulfonate salt according to the invention, a formulator using such a salt is able to reap added benefit from the presence of both a cationic surfactant and an anionic surfactant in the same solid material, which may be powdered. Such salts therefore may reduce the costs associated with storage and blending of different materials, as is currently common in the art owing to the presence of both a surfactant and a detergent in the same molecule.

Owing to the unexpected finding that certain salts of the alkylbenzene sulfonates having sufficient 2-phenyl isomer content are solids at room temperature, the present invention also comprises as formulations useful for cleaning laundry which comprise solid tablets, as well as solid bars of soap comprising the solid alkylbenzene sulfonates as an active detergent component.

Detergent tablets are described, for example, in GB 911 204 (Unilever), U.S. Pat. No. 3,953,350 (Kao), JP 60 015 500A (Lion), JP 60 135 497A (Lion) and JP 60 135 498A (Lion); and are sold commercially in Spain. Detergent tablets are generally made by compressing or compacting a detergent powder, as is well-known in the art. Thus, the present invention contemplates substitution of at least a portion of, and more preferably all of, the active detergent component of a conventional laundry tablet of the prior art with a salt of an alkylbenzene sulfonate having sufficiently high 2-phenyl isomer to cause such salt to exist in the form of a solid at room temperature. Such substitution is readily made by providing such solid sulfonate in the stead of the conventional detergent component of the conventional laundry tablet during laundry tablet manufacture.

Bars of soap are made by various means known to those in the art including the pouring into molds of a caustic/oil mixture prior to its full saponification, or the use of "soap noodles" in a press with or without the aid of heat and pressure. Soaps typically include fatty acid carboxylates, perfumes, dyes, preservatives, bactericides, fillers such as talc, and other additives. The present invention contemplates substitution of at least a portion of, and more preferably all of, the active cleaning component of a conventional bar of soap of the prior art with a salt of an alkylbenzene sulfonate having sufficiently high 2-phenyl isomer to cause such salt to exist in the form of a solid at room temperature. Such substitution is readily made by providing such solid sulfonate in the stead of the conventional detergent component of the conventional bar of soap during soap manufacture. Thus, a bar of soap according to the invention may comprise only the Super High 2-phenyl alkylbenzene sulfonate according to the invention, in combination with sufficient binders, perfumes, dyes, etc. to form a solid bar of soap, using in one form of the invention the same general compression techniques useful for producing laundry tablets.

Although the present invention has been shown and described with respect to certain preferred embodiments, it is obvious that equivalent alterations and modifications will occur to others skilled in the art upon the reading and understanding of the specification. The present invention includes all such equivalent alterations and modifications, and is limited only by the scope of the claims appended hereto. Although the processes used to make the products claimed herein have been described as employing olefin and paraffin feedstocks which are generally linear in molecular configuration, it is appreciated by those skilled in the art that commercial grade linear olefinic and paraffinic feedstocks typically contain incidental and sometimes non-incidental attendant quantities of non-linear olefins and paraffins, which may show up in an alkylbenzene produced by a process described by the present invention as a substrate which is part of a non-linear alkylbenzene, either by direct reaction, or by isomerizations which inevitably occur during processes of the general types of reactions described herein, as recognized by those skilled in the art.

What is claimed is:

1. A composition useful as a detergent for cleaning laundry, dishes, hard surfaces, and other substrates that is formed from components comprising:
   a) an alkylbenzene sulfonate surfactant component present in any amount between 0.25% and 99.50% by weight based upon the total weight of the composition, said component characterized as comprising any amount between 42.00% and 85.00% by weight based upon the total weight of the component, including every hundredth percentage therebetween, of water-soluble sulfonates of the 2-phenyl isomers of alkylbenzenes described by the general formula:

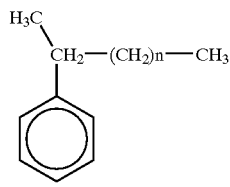

wherein n is equal to any integer between 4 and 18; and
   b) any amount between 99.75% and 0.50% of a second component that comprises at least one material selected from the group consisting of: a fatty acid, an alkyl sulfate, an ethanolamine, an amine oxide, an alkali carbonate, water, a $C_1$ to $C_6$ alcohol, pine oil, sodium chloride, sodium silicate, a water-soluble polymer having a weight-average molecular weight of at least 1000, an alcohol alkoxylate, a zeolite, a perborate salt, an alkali sulfate, an enzyme, a hydrotrope, a dye, a fragrance, a preservative, a brightener, a builder, a polyacrylate, an essential oil, an alkali hydroxide, a water-soluble branched alkylbenzene sulfonate, an ether sulfate, an alkylphenol alkoxylate, a fatty acid amide, an alpha olefin sulfonate, a paraffin sulfonate, a betaine, a chelating agent, a tallowamine ethoxylate, a polyetheramine ethoxylate, an ethylene oxide/propylene oxide block copolymer, an alcohol ethylene oxide/propylene oxide surfactant, a methyl ester sulfonate, an alkyl polysaccharide, an N-methyl glucamide, an alkylated sulfonated diphenyl oxide, a polyethylene glycol, and a water soluble alkylbenzene sulfonate having a 2-phenyl isomer content of less than 30.00%.

2. A composition according to claim 1 wherein the 2-phenyl isomers content of the alkylbenzene sulfonate surfactant component comprises any amount between 47.00% and 70.00% by weight based upon the total weight of the component, including every hundredth percentage therebetween.

3. A composition according to claim 1 wherein the alkylbenzene sulfonate surfactant component that is present in any amount between 0.25% and 99.50% by weight, and which is characterized as comprising any amount between 42.00% and 85.00% by weight of water-soluble sulfonates of said 2-phenyl isomers, itself comprises a mixture of linear alkylbenzene sulfonates and branched alkylbenzene sulfonates, wherein the linear alkylbenzene sulfonates of said mixture comprise five different sulfonates of the alkylbenzenes described by said general formula with five different n values, and wherein said n values are selected from integers in the range between 4 and 18.

4. A composition according to claim 1 wherein the alkylbenzene sulfonate surfactant component that is present in any amount between 0.25% and 99.50% by weight, and which is characterized as comprising any amount between 42.00% and 85.00% by weight of water-soluble sulfonates of said 2-phenyl isomers, itself comprises a mixture of linear alkylbenzene sulfonates and branched alkylbenzene sulfonates, wherein the branched alkylbenzene sulfonates of said mixture comprise at least 5 different sulfonates of the alkylbenzenes described by said general formula with five different n values, and wherein said n values are selected from integers in the range between 4 and 18.

5. A composition according to claim 3 wherein the branched alkylbenzene sulfonates of said mixture comprise at least 5 different sulfonates of the alkylbenzenes described by said general formula with five different n values, and wherein said n values are selected from integers in the range between 4 and 18.

6. A composition according to claim 1 wherein said alkylbenzene sulfonate surfactant component is present in any amount between 1.00% and 25.00% by weight based upon the total weight of said composition useful as a detergent, including every hundredth percentage therebetween.

7. A composition according to claim 1 wherein said second component is present in any amount between 0.10% and 25.00% by weight based upon the total weight of said composition useful as a detergent.

8. A composition according to claim 1 further comprising a third component, wherein said third component is different from said second component and is selected from the group consisting of: fatty acids; alkyl sulfates; an ethanolamine; an amine oxide; alkali carbonates; water; ethanol; isopropanol; pine oil; sodium chloride; sodium silicate; polymers; alcohol alkoxylates; zeolites; perborate salts; alkali sulfates; enzymes; hydrotropes; dyes; fragrances; preservatives; brighteners; builders; polyacrylates; essential oils; alkali hydroxides; water-soluble branched alkylbenzene sulfonates; water-soluble substantially linear alkylbenzene sulfonates having a 2-phenyl isomer content of less than 30.00%; water-soluble branched alkylbenzene sulfonates having a 2-phenyl isomer content of less than 30.00%; water-soluble substantially linear alkylbenzene sulfonates having a 2-phenyl isomer content of greater than 30.00%; and water-soluble branched alkylbenzene sulfonates having a 2-phenyl isomer content of greater than 30.00%.

9. A composition according to claim 8 wherein said third component is a mixture of branched and substantially linear water-soluble alkylbenzene sulfonates wherein said water-soluble alkylbenzene sulfonates have a 2-phenyl isomer content of less than 25.00% by weight based upon the total weight of said water soluble alkylbenzene sulfonate component.

10. A composition according to claim 8 wherein said third component is a mixture of branched and substantially linear water-soluble alkylbenzene sulfonates wherein said water-soluble alkylbenzene sulfonates have a 2-phenyl isomer content of grater than 25.00% by weight based upon the total weight of said water soluble alkylbenzene sulfonate component.

11. A composition as in claim 8 wherein the alkylbenzene sulfonate surfactant component contains an effective amount of 2-phenyl isomer to provide a turbidity in a cleaning solution formed from mixing said composition and water of below 200 NTU units when the total hardness level of the water is any value between 100–300 ppm, and the alkylbenzene sulfonate surfactant concentration in the cleaning solution is any amount between 0.09 and 0.11%.

12. A salt comprising a mixture of at least 5 different alkylbenzene sulfonates wherein 1.00% to 30.00% of the alkyl groups bonded to the benzene ring in said alkylbenzene sulfonates are substantially linear and have any number of carbon atoms selected from the group consisting of 10, 11, 12, 13, and 14, and wherein said salt comprises an effective amount of 2-phenyl isomers for rendering said salt to exist in the form of a solid at room temperature.

13. A salt comprising a mixture of at least 5 different alkylbenzene sulfonates wherein 30.00% to 50.00% of the alkyl groups bonded to the benzene ring in said alkylbenzene sulfonates are substantially linear and have any number of carbon atoms selected from the group consisting of: 10, 11, 12, 13, and 14, and wherein said salt comprises an effective amount of 2-phenyl isomers for rendering said salt to exist in the form of a solid at room temperature.

14. A salt comprising a mixture of at least 5 different alkylbenzene sulfonates wherein 50.00–75.00% of the alkyl groups bonded to the benzene ring in said alkylbenzene sulfonates are substantially linear and have any number of carbon atoms selected from the group consisting of: 10, 11, 12, 13, and 14, and wherein said salt comprises an effective amount of 2-phenyl isomers for rendering said salt to exist in the form of a solid at room temperature.

15. A salt comprising a mixture of at least 5 different alkylbenzene sulfonates wherein 75.00–95.00% of the alkyl groups bonded to the benzene ring in said alkylbenzene sulfonates are substantially linear and have any number of carbon atoms selected from the group consisting of: 10, 11, 12, 13, and 14, and wherein said salt comprises an effective amount of 2-phenyl isomers for rendering said salt to exist in the form of a solid at room temperature.

16. A salt comprising a mixture of at least 5 different alkylbenzene sulfonates wherein 1.00% to 30.00% of the alkyl groups bonded to the benzene ring in said alkylbenzene sulfonates are branched and have any number of carbon atoms selected from the group consisting of: 10, 11, 12, 13, and 14, and wherein said salt comprises an effective amount of 2-phenyl isomers for rendering said salt to exist in the form of a solid at room temperature.

17. A salt comprising a mixture of at least 5 different alkylbenzene sulfonates wherein 30.00% to 50.00% of the alkyl groups bonded to the benzene ring in said alkylbenzene sulfonates are branched and have any number of carbon atoms selected from the group consisting of 10, 11, 12, 13, and 14, and wherein said salt comprises an effective amount of 2-phenyl isomers for rendering said salt to exist in the form of a solid at room temperature.

18. A salt comprising a mixture of at least 5 different alkylbenzene sulfonates wherein 50.00–75.00% of the alkyl groups bonded to the benzene ring in said alkylbenzene sulfonates are branched and have any number of carbon atoms selected from the group consisting of: 10, 11, 12, 13, and 14, and wherein said salt comprises an effective amount of 2-phenyl isomers for rendering said salt to exist in the form of a solid at room temperature.

19. A salt comprising a mixture of at least 5 different alkylbenzene sulfonates wherein 75.00–95.00% of the alkyl groups bonded to the benzene ring in said alkylbenzene sulfonates are branched and have any number of carbon atoms selected from the group consisting of: 10, 11, 12, 13, and 14, and wherein said salt comprises an effective amount of 2-phenyl isomers for rendering said salt to exist in the form of a solid at room temperature.

* * * * *